(12) United States Patent
Sibary et al.

(10) Patent No.: US 11,738,193 B2
(45) Date of Patent: Aug. 29, 2023

(54) BARRIERS FOR ELECTRODES

(71) Applicant: Cochlear Limited, Macquarie University (AU)

(72) Inventors: Peter Raymond Sibary, Macquarie University (AU); Nicholas Charles Pawsey, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1072 days.

(21) Appl. No.: 15/337,025

(22) Filed: Oct. 28, 2016

(65) Prior Publication Data

US 2018/0117310 A1    May 3, 2018

(51) Int. Cl.
*A61N 1/05* (2006.01)
*A61N 1/36* (2006.01)

(52) U.S. Cl.
CPC ....... *A61N 1/0541* (2013.01); *A61N 1/36036* (2017.08); *A61N 1/36038* (2017.08)

(58) Field of Classification Search
CPC .................................................. A61N 1/0541
See application file for complete search history.

(56) References Cited

U.S. PATENT DOCUMENTS

| | | | |
|---|---|---|---|
| 6,112,124 A | 8/2000 | Loeb | |
| 6,862,805 B1 | 3/2005 | Kuzma et al. | |
| 7,949,412 B1* | 5/2011 | Harrison | A61N 1/0541 607/136 |
| 8,792,999 B2 | 7/2014 | Sibary et al. | |
| 2004/0127968 A1 | 7/2004 | Kuzma et al. | |
| 2006/0287689 A1* | 12/2006 | Debruyne | A61P 41/00 607/57 |
| 2008/0154339 A1 | 6/2008 | Carter | |
| 2011/0178587 A1* | 7/2011 | Chambers | A61N 1/0541 607/137 |
| 2011/0288468 A1* | 11/2011 | Dadd | A61M 31/002 604/21 |
| 2011/0301681 A1 | 12/2011 | Risi | |
| 2012/0004715 A1 | 1/2012 | Ramachandran et al. | |
| 2014/0303548 A1 | 10/2014 | Jolly et al. | |
| 2015/0073520 A1 | 3/2015 | Strahl et al. | |

(Continued)

FOREIGN PATENT DOCUMENTS

| | | |
|---|---|---|
| CN | 102958562 A | 3/2013 |
| CN | 105102058 A | 11/2015 |
| CN | 105658272 A | 6/2016 |

(Continued)

OTHER PUBLICATIONS

International Search Report and Written Opinion for PCT/IB2017/056570, dated Feb. 13, 2018.

(Continued)

*Primary Examiner* — Rex R Holmes
*Assistant Examiner* — Jennifer L Ghand
(74) *Attorney, Agent, or Firm* — Pilloff Passino & Cosenza LLP; Martin J. Cosenza

(57) ABSTRACT

A method, including providing an electrical current to an electrode contact located in a cochlea of a human to evoke a hearing percept, and managing flow of perilymph located inside the cochlea locally to the electrode contact while the current is provided to the electrode contact. In an exemplary embodiment, the management is executed using a seal.

29 Claims, 31 Drawing Sheets

(56) References Cited

U.S. PATENT DOCUMENTS

2016/0059014 A1 3/2016 Johnston et al.
2016/0213913 A1 7/2016 Dhanasingh et al.

FOREIGN PATENT DOCUMENTS

| EP | 3017842 A1 | 5/2016 | |
|---|---|---|---|
| JP | H11502441 A | 3/1999 | |
| KR | 100859979 B1 | 9/2008 | |
| WO | 9631087 A1 | 10/1996 | |
| WO | WO-2015034981 A1 * | 3/2015 | ........... A61N 1/0541 |

OTHER PUBLICATIONS

Office Action for China Patent Application No. 201780066857.5, dated Oct. 22, 2020.
Office Action for China Patent Application No. 201780066857.5, dated Jun. 4, 2021.

\* cited by examiner

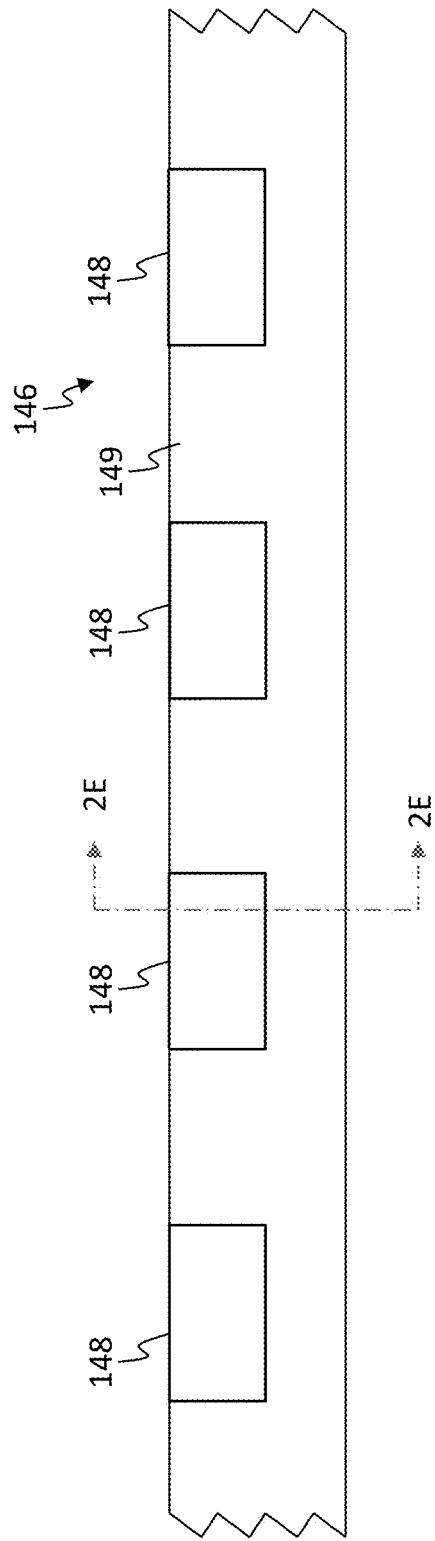
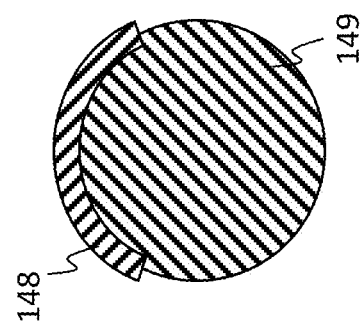
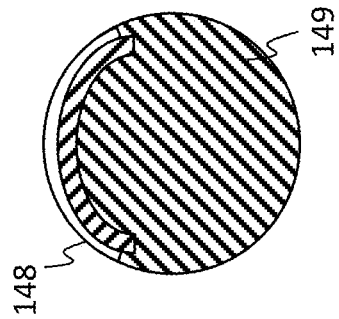
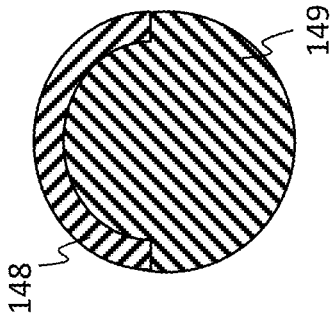
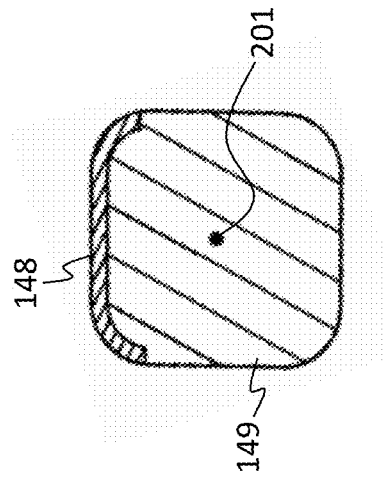

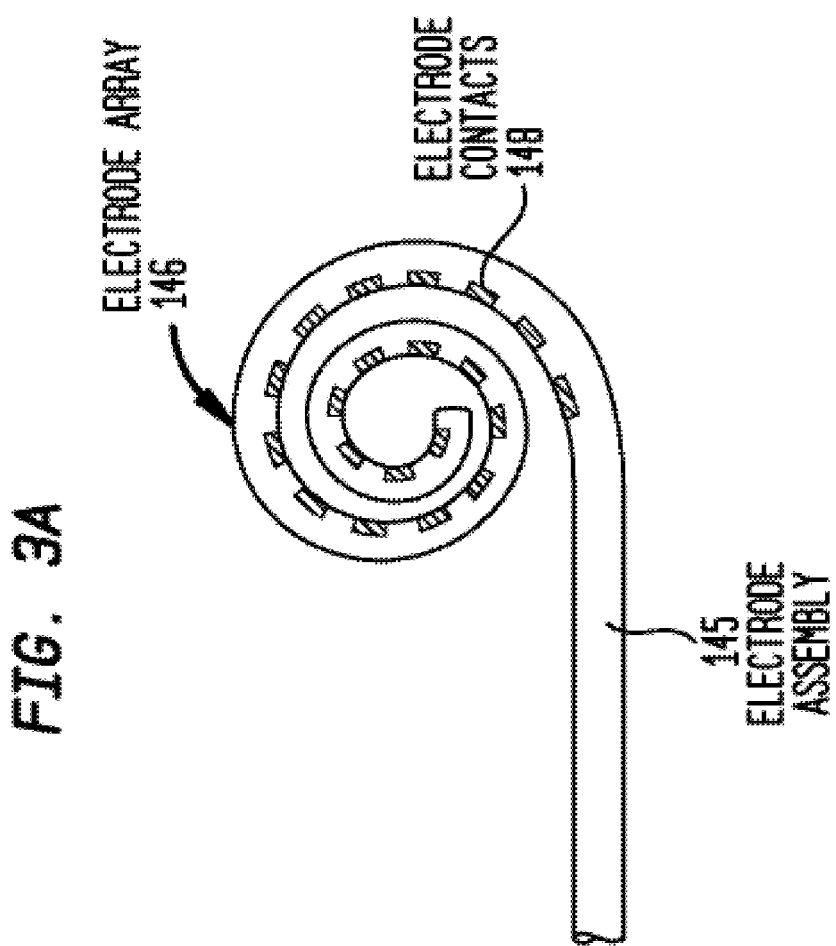

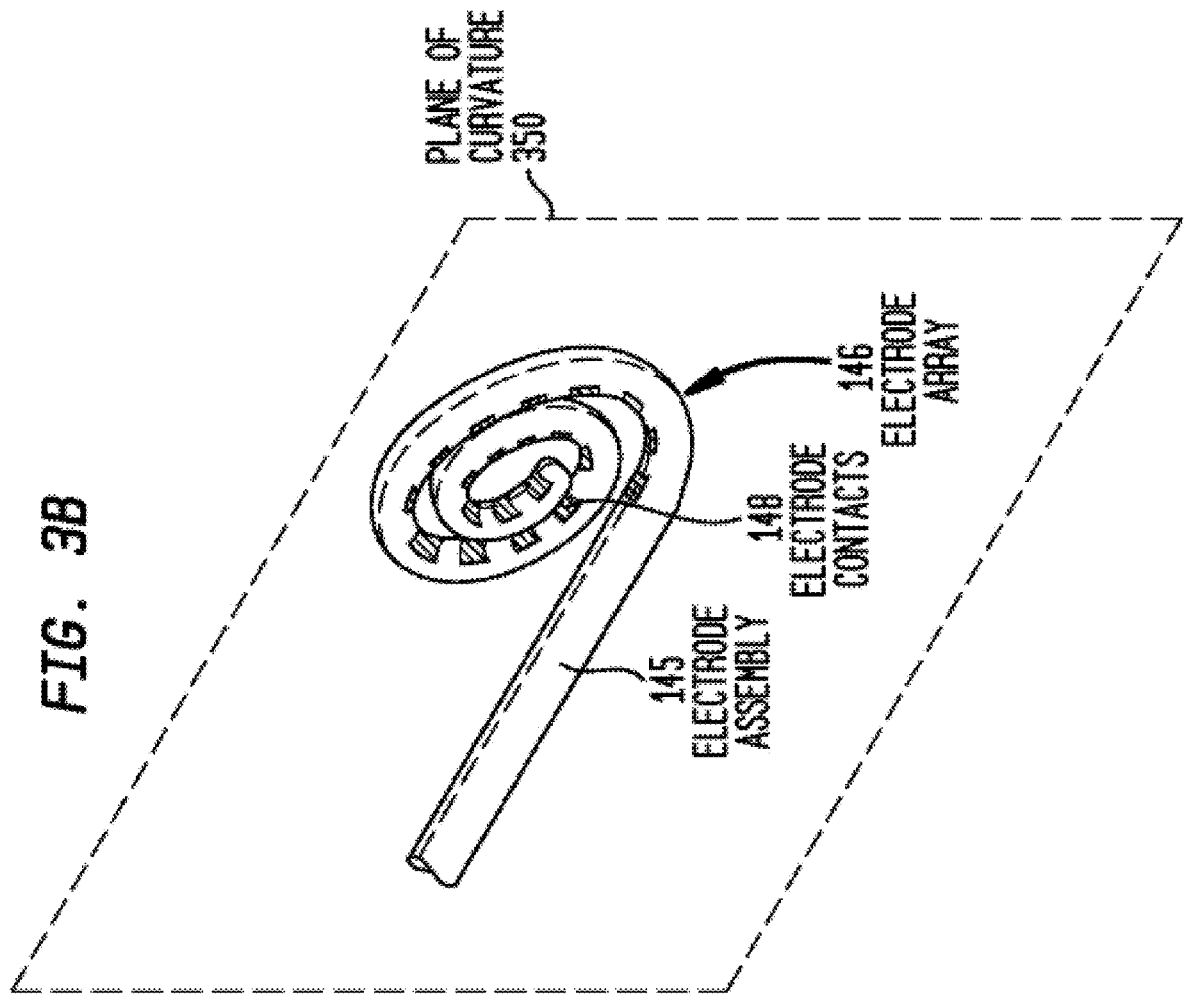

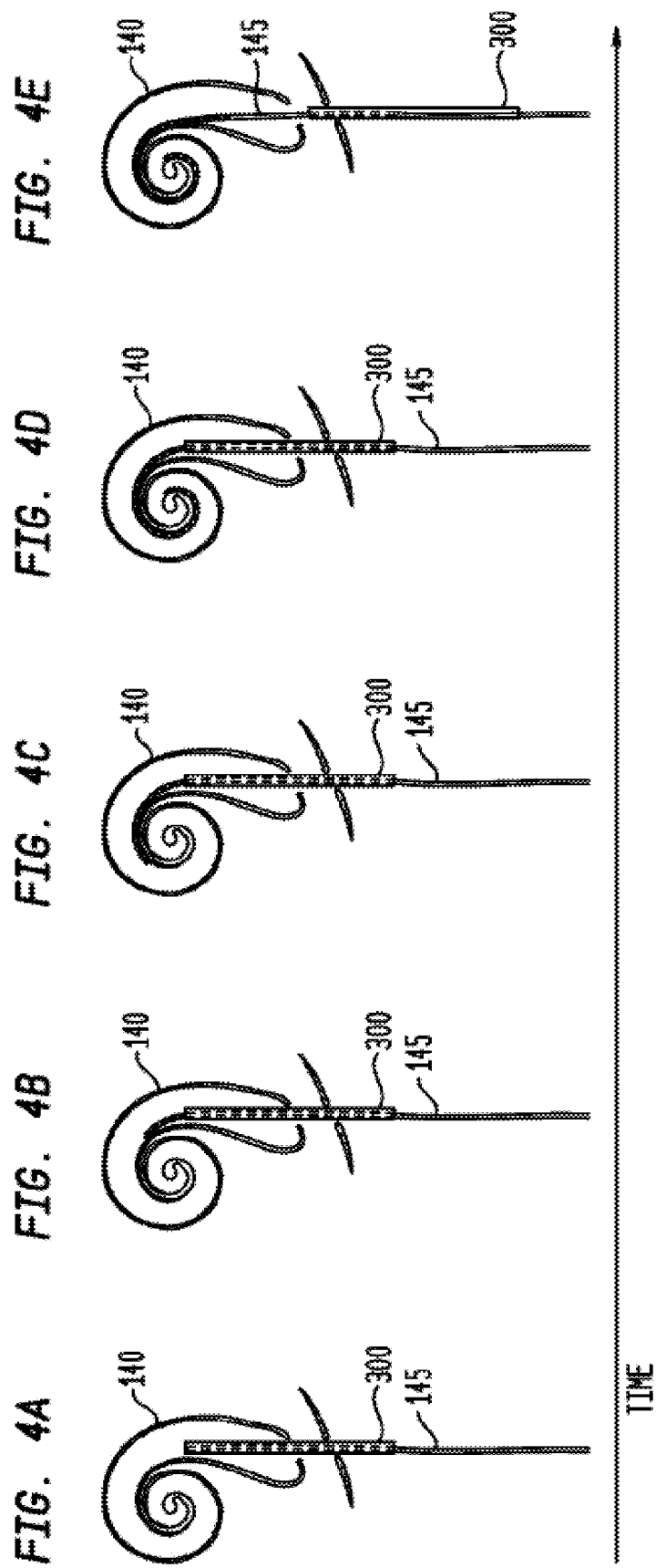

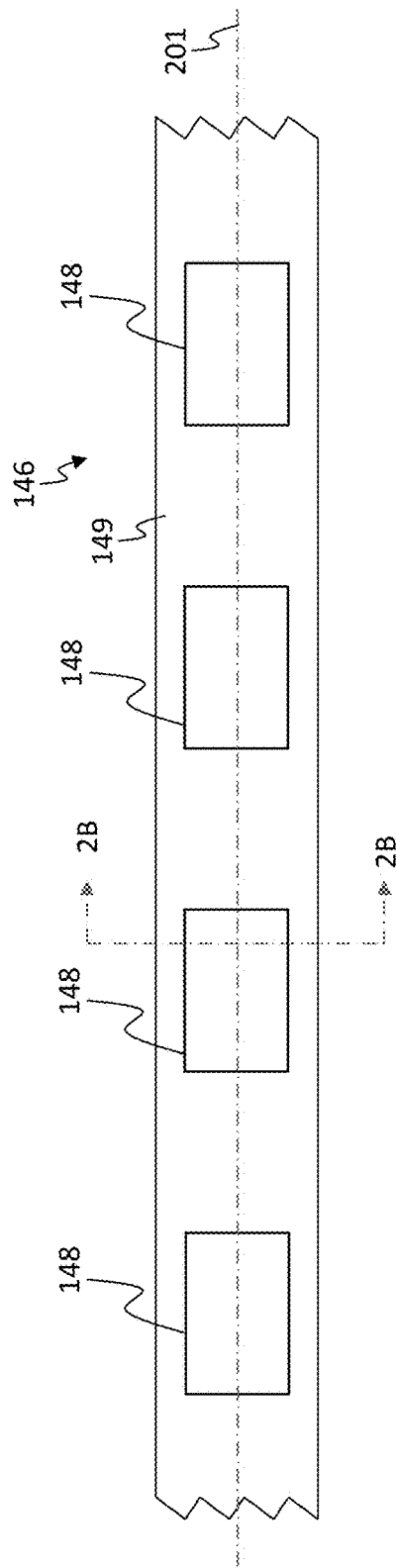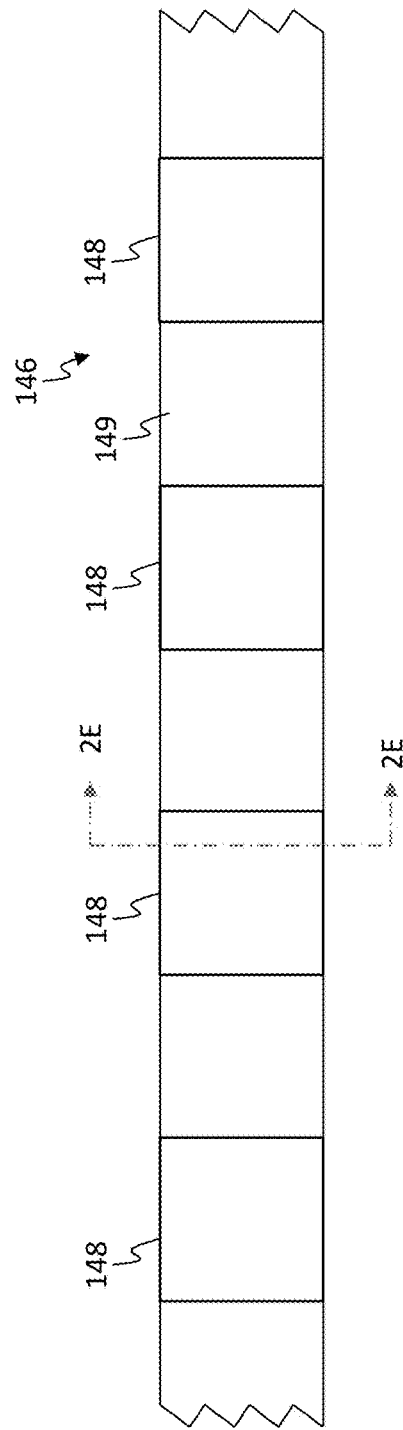

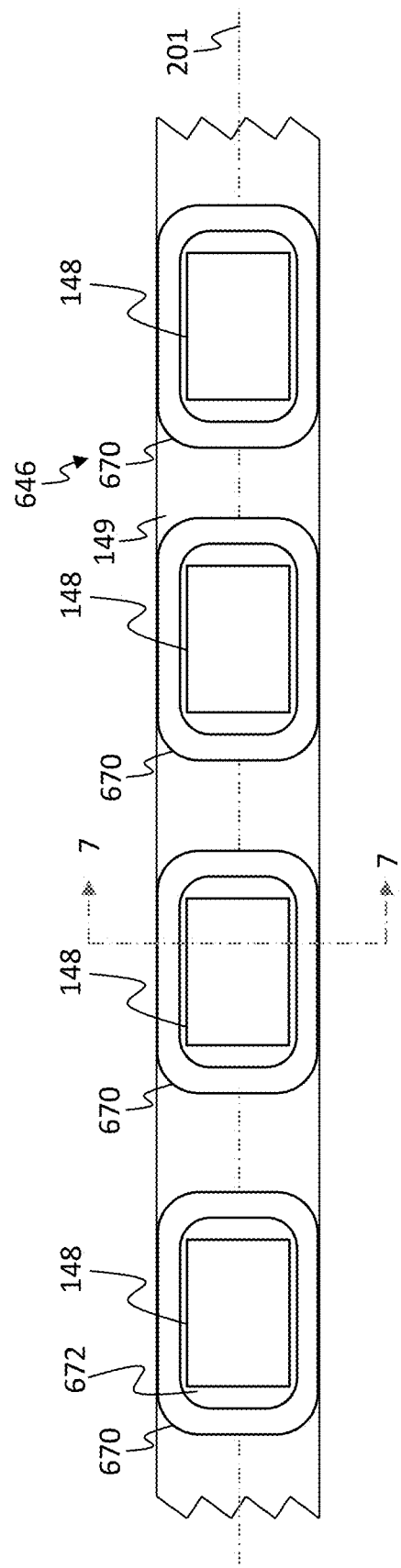

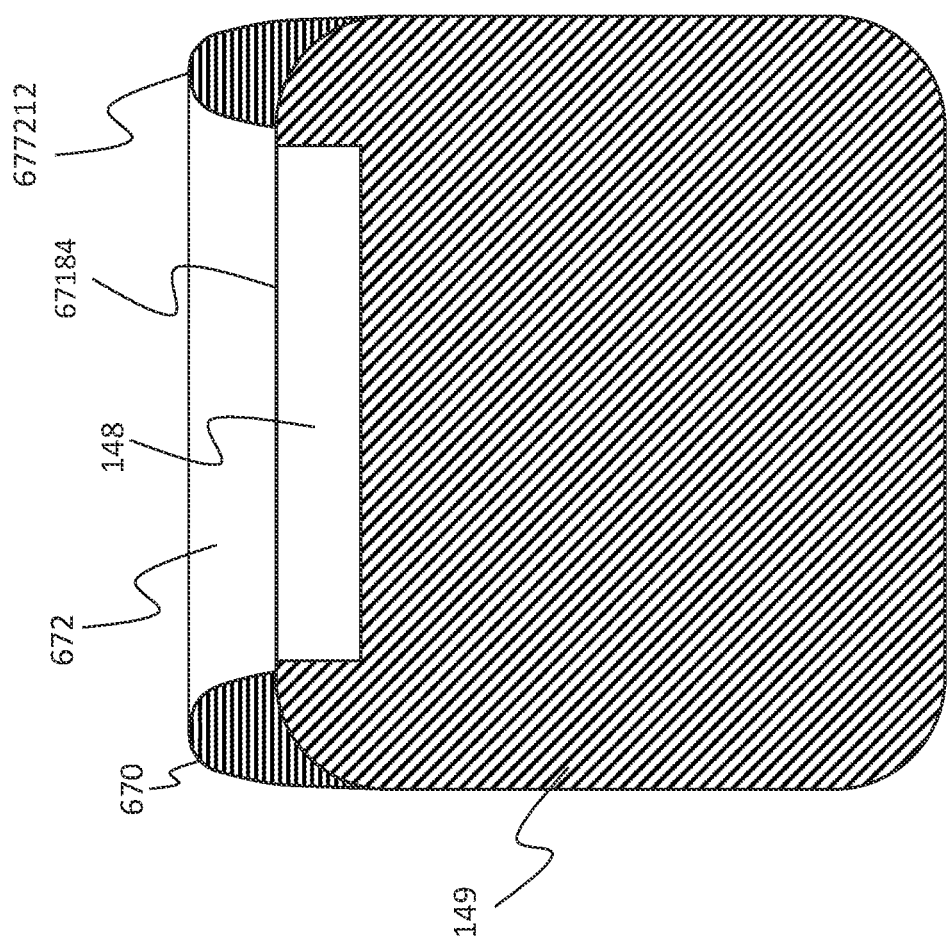

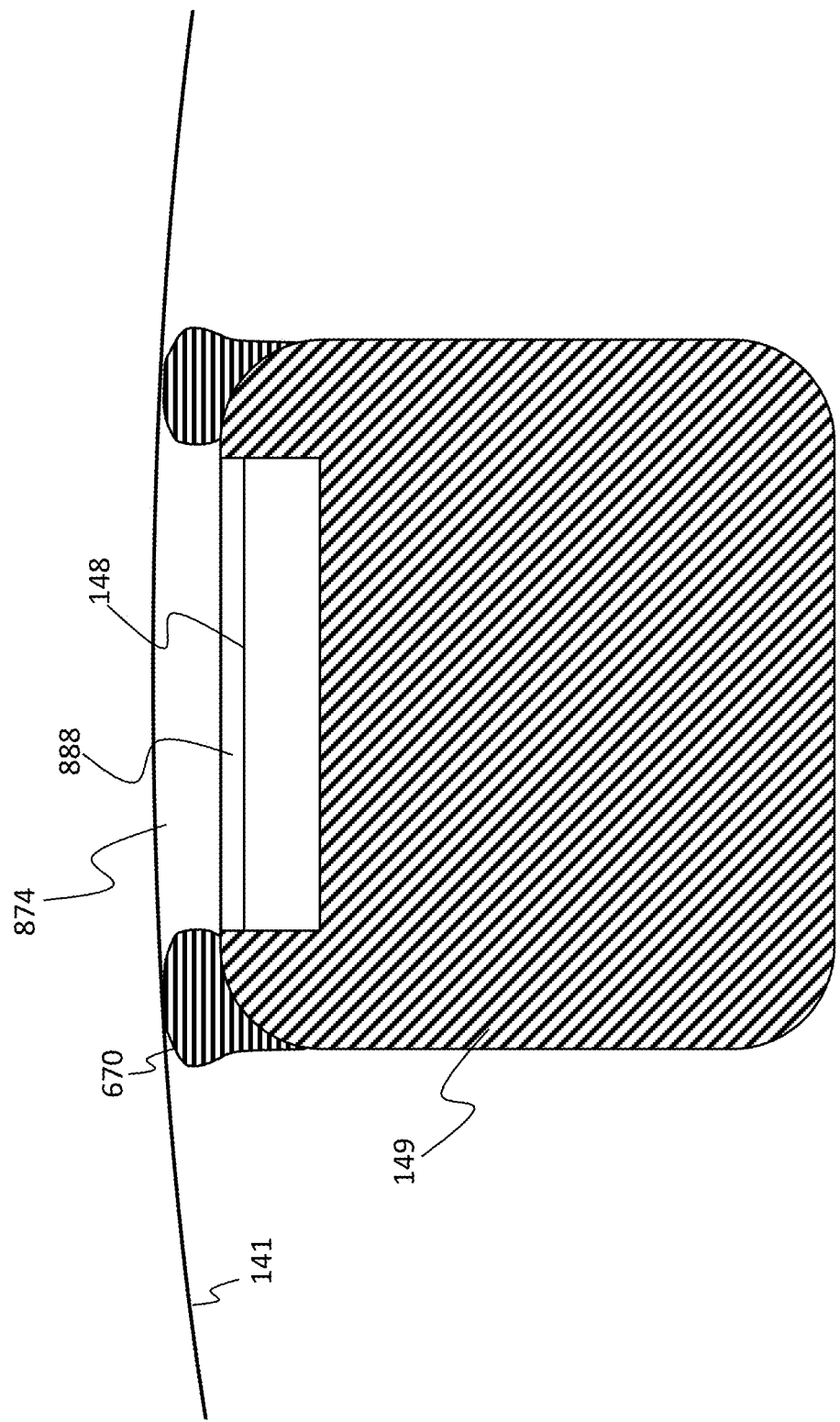

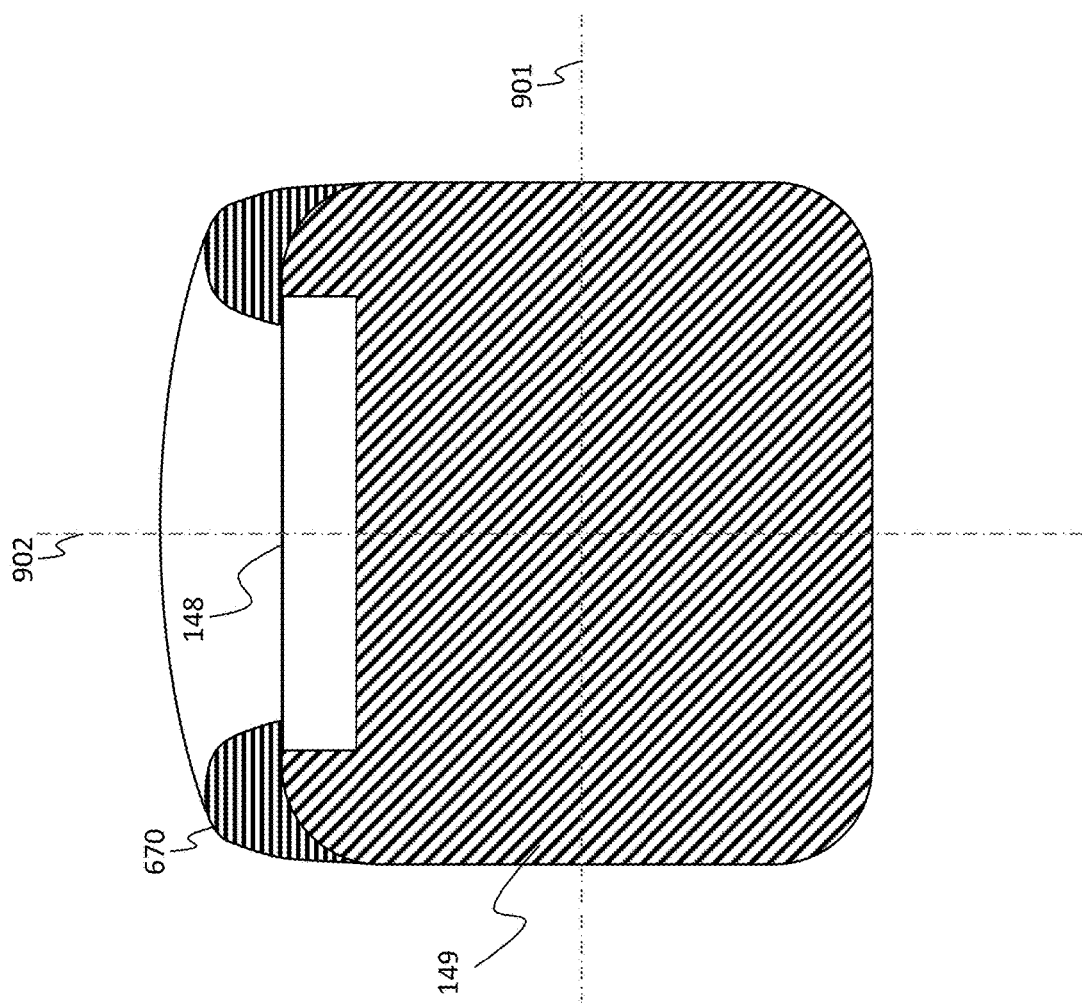

BARRIERS FOR ELECTRODES

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is also noted that the electrode array of the cochlear implant generally shows utilitarian results if it is inserted in a cochlea.

SUMMARY

In accordance with an exemplary embodiment, there is an implantable stimulating assembly, comprising, and an electrode contact, an electrode carrier member; and a barrier extending about the electrode contact on an outside of the carrier member.

In accordance with another exemplary embodiment, there is a cochlear electrode array, comprising, an array of electrode contacts, a carrier carrying the array of electrode contacts, and respective barriers surrounding the electrode contacts.

In accordance with another exemplary embodiment, there is a method, comprising providing an electrical current to an electrode contact located in a cochlea of a human to evoke a hearing percept, and managing flow of perilymph located inside the cochlea locally to the electrode contact while the current is provided to the electrode contact.

In accordance with another exemplary embodiment, there is method, comprising providing an electrical current to an electrode contact located in a cochlea of a human to evoke a hearing percept, the electrode contact being part of an electrode array of a cochlear implant, transferring at least a portion of the applied current to a wall of the cochlea proximate the electrode contact, and limiting current spread in a majority of directions parallel to a tangent surface of the electrode contact at a location midway between the surface and the wall of the cochlea.

BRIEF DESCRIPTION OF THE DRAWINGS

Embodiments are described below with reference to the attached drawings, in which:

FIGS. 2A-2H are views of exemplary electrode arrays to which the teachings detailed herein can be applicable;

FIGS. 3A and 3B are side and perspective views of an electrode assembly extended out of an embodiment of an insertion sheath of the insertion tool illustrated in FIG. 2;

FIGS. 4A-4E are simplified side views depicting an exemplary insertion process of the electrode assembly into the cochlea;

FIGS. 5A and 5B are exemplary top views of electrode arrays;

FIG. 6 is an exemplary top view of an exemplary array according to an embodiment;

FIGS. 7 to 12 are exemplary cross-sections of some exemplary electrode arrays according to some exemplary embodiments, and variously include some structures of the cochlea;

DETAILED DESCRIPTION

Figure 1:
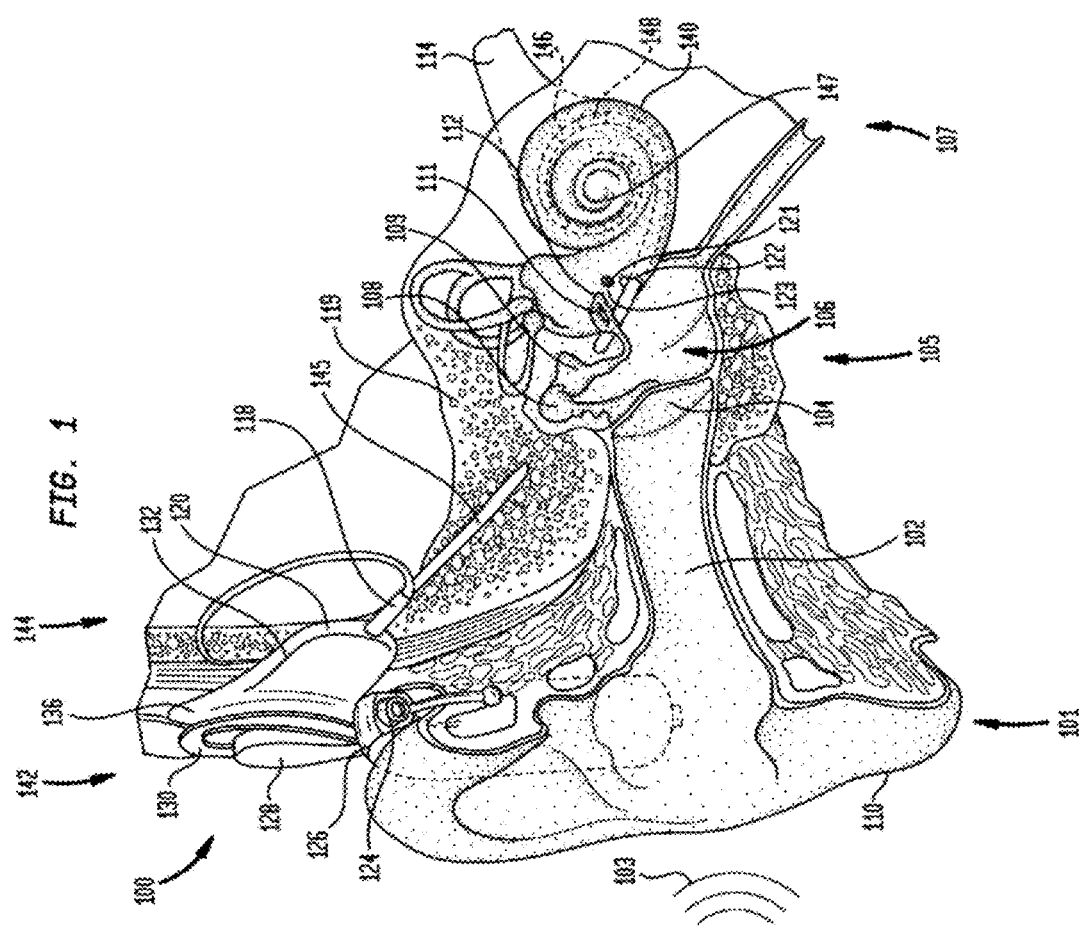
FIG. 1 is a perspective view of an exemplary hearing prosthesis.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially-implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Figure 2A:
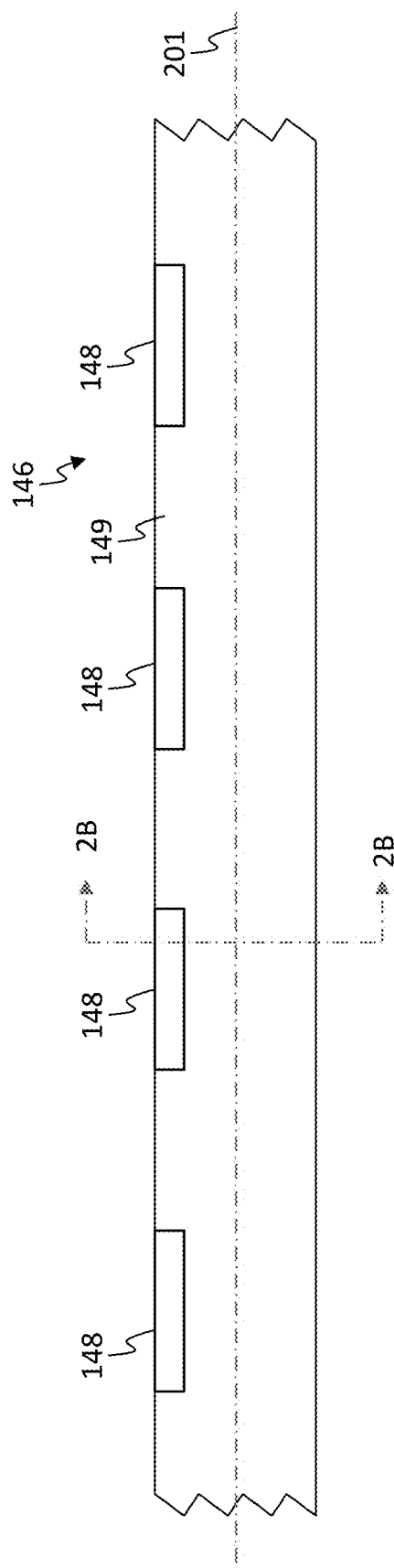
Figure 2C:
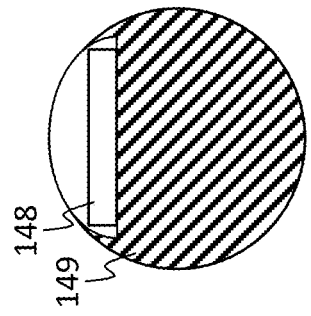
Figure 2B:
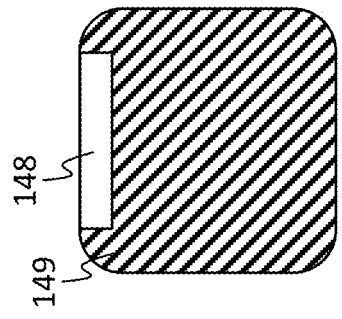

FIG. 2A depicts a conceptual side view of a portion of electrode array 146, depicting four electrode contacts 148 evenly spaced along a longitudinal axis of the electrode array 146. It is noted that in some alternate embodiments, the electrode is not evenly spaced. FIG. 2B depicts a conceptual cross-sectional view through one of the electrode contacts 148, which also depicts the carrier 149 of the electrode contact 148. In an exemplary embodiment, the carrier 149 is made of silicone. Not depicted in the figures are electrical leads and stiffener components that are sometimes embedded in the carrier 149. The embodiment of FIG. 2B represents an electrode array 146 that has a generally rectangular cross-section. FIG. 2C depicts an alternate embodiment where the electrode array 146 has a generally circular cross-section. It is also noted that in some exemplary embodiments, the cross-section is oval shaped. Thus, the embodiment of FIGS. 2A-2C is a species of the genus of an electrode array having a generally continuously curving cross-section. Any electrode array of any cross-section or any configuration can be utilized with the teachings detailed herein.

The electrode contacts 148 depicted in FIGS. 2A-2C are so-called flat contacts. In this regard, the surface of the electrode contact that faces the wall of the cochlea/the faces away from the longitudinal axis of the electrode array 146 is flat. Conversely, as seen in FIGS. 2D-2H, in some alternate embodiments, the electrode contacts 148 are so-called half band electrodes. In some exemplary embodiments, a band of contact material is "smashed" or otherwise compressed into a "half band," as seen in the figures. It is noted that by "half band," this does not mean that the electrode contact must necessarily span half of the outside diameter of the electrode array, as is the case in FIGS. 2G and 2H. The term is directed towards the configuration of the electrode itself as that term has meaning in the art. Any electrode contact that can have utilitarian value according to the teachings detailed herein can be utilized in at least some exemplary embodiments.

As can be seen from FIGS. 2A-2H, the positioning of the electrode contacts relative to the carrier 149 can vary with respect to alignment of the outer surface of the carrier with the outer surface of the contact. For example, FIGS. 2A, 2E, and 2F depict the outer surface of the contacts 148 as being flush with the outer surface of the carrier 149. Conversely, FIGS. 2C and 2G depict the contact 148 as being recessed with respect to the outer surface of the carrier 149, while FIG. 2H depicts the contact 148 as being proud relative to the outer surface of the contact 149. It is noted that these various features are not limited to the specific contact geometry and/or the specific carrier geometry depicted in the figures, and that one or more features of one exemplary embodiment can be combined with one or more features of another exemplary embodiment. For example, while FIG. 2H depicts a half band contact as being proud of the carrier 149 having a generally circular cross-section, a flat electrode such as that depicted in FIG. 2A can be proud of the carrier as well.

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that the teachings detailed herein and/or variations thereof can be applicable to a so-called straight electrode array, which electrode array does not curl after being free of a stylet or insertion guide tube etc., but instead remains straight.

The perimodiolar electrode assembly 145 of FIGS. 3A and 3B is pre-curved in a direction that results in electrode contacts 148 being located on the interior of the curved assembly, as this causes the electrode contacts to face the modiolus when the electrode assembly is implanted in or adjacent to cochlea 140.

It is also noted that while the embodiments of FIGS. 2A-3B have been presented in terms of a so-called non-tapered electrode array (where the cross-sections of the array on a plane normal to the longitudinal axis at various locations along the longitudinal axis (e.g. in between each electrode (or a majority of the electrodes), in the middle of each electrode (or a majority of the electrodes) etc.) have generally the same cross-sectional area and shape), in an alternate embodiment, the teachings detailed herein can be applicable to a so-called tapered electrode, where the cross-sectional areas on planes taken normal to the longitudinal axis decrease with location towards the distal end of the electrode array.

FIGS. 4A-4E depict an exemplary insertion regime of an electrode assembly according to an exemplary embodiment. As shown in FIG. 4A, the combined arrangement of an insertion guide tube 300 and electrode assembly 145 is substantially straight. This is due in part to the rigidity of insertion guide tube 300 relative to the bias force applied to the interior wall of the guide tube by pre-curved electrode assembly 145.

As noted, in some embodiments, the electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. In the embodiment configured to be implanted in scala tympani of the cochlea, electrode assembly 145 is pre-curved to have a radius of curvature that approximates and/or is less than the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

FIG. 5A depicts a top view of the electrode array of FIG. 2A (looking downward from the top with respect to the frame of reference of FIG. 2A. FIG. 5B depicts a top view of the electrode array of FIG. 2D (again, looking downward from the top with respect to the frame of reference of FIG. 2D). It is noted that while the embodiment of FIG. 5A depicts the flat electrode contacts as having a width (the dimension normal to the longitudinal axis 201 with respect to the frame of reference of FIG. 5A) that is less than the width (again, the dimension normal to the longitudinal axis 201 with respect to the frame of reference of FIG. 5A) of the carrier 149, in some other embodiments, the width of the flat electrode contacts can be equal to and/or greater than the width of the carrier 149 (e.g., FIG. 5B can be representative of an array of flat electrode contacts). Note also that while the embodiment depicted in FIG. 5A depicts a length (the dimension parallel to the longitudinal axis 201 with respect to the frame of reference of FIG. 5A) of the electrode contacts that is longer than that of the width, in an alternate embodiment, the length can be the same and/or less than the width.

It is noted that while the embodiment of FIG. 5B depicts the half band electrode contacts as having a width that is equal to the width of the carrier 149, in some other embodiments, the width of the half band electrode contacts can be less than and/or greater than the width of the carrier 149. Indeed, in an exemplary embodiment, the representation of FIG. 5A can be representative of the half band electrode arrangement (e.g., the cross section 2B could correspond to FIG. 2G). Note also that while the embodiment depicted in FIG. 5B depicts a length of the electrode contacts that is equal to the width, in an alternate embodiment, the length can be greater than and/or less than the width.

In an exemplary embodiment where barriers are utilized in conjunction with the carrier (either as a separate component or as part of the carrier) will now be described.

More particularly, FIG. 6 depicts an exemplary electrode array 646 that includes a seal 670 that extends about the contact 148. In this exemplary embodiment, there is an electrode array 646 configured to sit against a wall of the cochlear duct, which electrode array has sealing features around respective individual electrode contacts. The seal seals against the wall of the cochlea to limit (including prevent) current flow away from the electrode contact through the perilymph. In an exemplary embodiment, the sealing features are flexible (compliant) in order to accommodate irregularity in the wall surface, curvature of the surface in two directions and mismatch between the electrode spiral shape and the cochlea's spiral, etc. In an exemplary embodiment, the sealing features deform to increase the contact area and so spread the contact force to reduce the pressure between the electrode array and the scala wall. In some embodiments, this can allow for greater contact force to be applied (balanced by the greater contact area), for more positive contact with the scala wall, without damaging the tissue through excessive chronic contact pressure relative to that which would be the case.

More particularly, the embodiment of FIG. 6 is a pre-curved perimodiolar electrode array with a superelastic nitinol inlay (not shown) designed to be more tightly curled than a small cochlea (human factors speaking—e.g., a $20^{th}$ percentile male or female cochlea (citizen of the United States, the United Kingdom, Republic of France, Federal Republic of Germany, Japan, People's Republic of China, etc., as applicable) and configured to adapt to a range of cochlea sizes by deforming with relatively minimal increase in reaction force. In this embodiment, the electrode contacts are planar (flat) and embedded in the modiolar side of the carrier 149.

As can be seen in FIG. 6, around the respective electrode contacts is a continuous lip of gel-like silicone rubber or foam that protrudes approximately 0.1-0.2 mm above the surface of the contact. In its final position in the cochlea, the silicone lips contact the modiolar wall and deform, producing a large contact area, and form a complete barrier around each contact to limit, including prevent, the flow of perilymph and electrical current, at least in a longitudinal direction. In at least some embodiments, the electrode array is configured such that the electrode pad is not in contact with the modiolus after final insertion. Instead, a volume of perilymph remains trapped within the space created by the lip seal through which current can flow from the electrode contact through the porous modiolar bone to the spiral ganglions of the cochlea.

In the embodiment of FIG. 6, the seal 670 is a rectangular-shaped seal that comprises a bed of gel-like silicon located on the top surface of the carrier 149. As will be described in greater detail below, other shapes of the seal can be utilized. For example, a circular shaped seal and/or an oval shaped seal can be utilized (these shapes are when viewed from the perspective of FIG. 6, the top/looking from the modiolar wall when the electrode array is inserted into the cochlea). As can be seen, in the relaxed state (and the view of FIG. 6 is in the relaxed state), the seal 670 is completely away from the electrode contact 148. As will be described in greater detail below, in some other embodiments, in the relaxed state, at least a portion of the seal can cover at least a portion of the electrode contact 148.

FIG. 7 depicts a cross-sectional view of the electrode array 146 depicted in FIG. 6. As can be seen, the seal 670 forms a space 672/valley 672 completely surrounding the electrode contact 148. The embodiment of FIG. 7 depicts the carrier 149 having a rectangular cross-section/generally rectangular cross-section. It is noted that the teachings detailed herein with respect to the seals can also be applied to carriers that utilize a curved cross-section (circular, oval, etc.) or any other cross-section that can have utilitarian value. Any arrangement of carrier that can be utilized with the teachings detailed herein can be utilized in at least some exemplary embodiments.

Note also that while the embodiments disclosed in the figures depict the seal as a separate component from the carrier (e.g., the combination of the seal and the carrier does not form a monolithic component), in other embodiments, the seal is simply an extension of the carrier/the seal and the remainder of the carrier are monolithic components. In an exemplary embodiment, the seal 670 is a lip seal which establishes a surface left on the surface of the carrier 149. In at least some exemplary embodiments, the seal is made of a soft durometer material, which material is softer than that of the carrier 149. Additional details of this will be described in greater detail below.

Figure 8A:
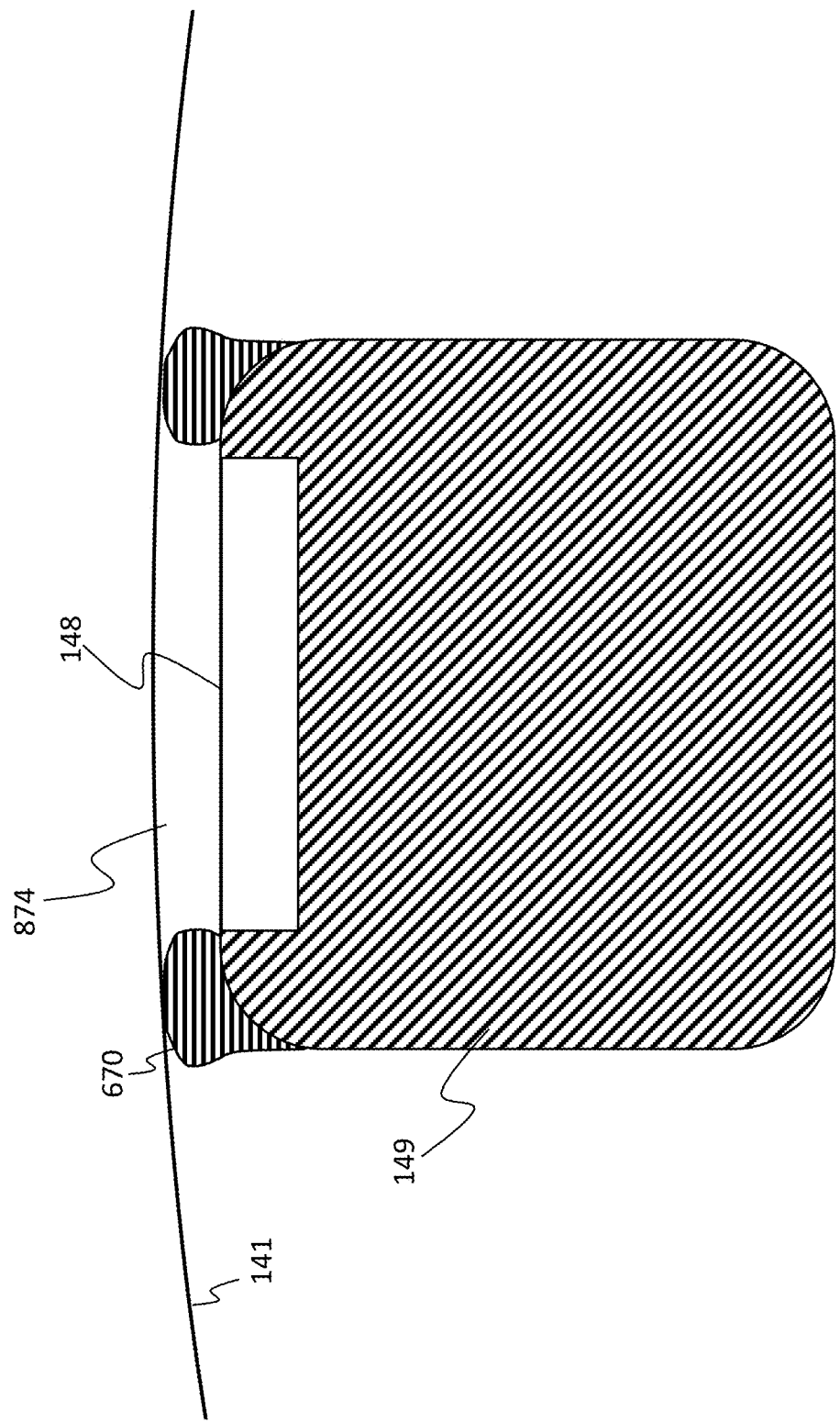

FIG. 8A depicts the view of FIG. 7 when the electrode array is located against the modiolus wall 141 of the cochlea 140. As can be seen, seal 670 is compressed in the vertical direction, and thus expands in the horizontal direction. As will be understood, owing to the curvature of the modiolus wall 141 of the cochlea, which curvature has a lower radius of curvature than that of the electrode array (when measured on the plane of FIG. 8A, some portions of the seal 670 will be more compressed than other portions). In this regard, the portions closer to the plane lying on the longitudinal axis that bifurcates the electrode contacts 148 and/or seal 670 into two even parts (e.g., an imaginary line on FIG. 8 extending vertically dividing the structure depicted in FIG. 8 in two even halves) can compress more or less depending on the structure of the electrode array and the seal. The electrode array that utilizes a rectangular cross-section carrier will experience more compression at the sides than at the center (relative to the frame of reference of FIG. 8A), while the electrode array that utilizes a circular cross-section carrier will experience more compression at the center than at the sides, all things being equal. That said, depending on the structure of the seal, this could be reversed and/or in some embodiments, the compression could be the same.

FIG. 8A depicts the resulting volume 874 that is established by the modiolus wall 141, the seal 670, the contact 148 (or, more accurately, the outside surface thereof), and the carrier 149, when the electrode array is fully inserted into the cochlea and is against the modiolus wall 141.

In an exemplary embodiment, the distance from the top surface of the electrode contact 148 to the topmost surface of the seal 670, in the relaxed state, and/or the average distance from the top surface of the electrode contact to the topmost surface of the seal 670, as measured in the vertical direction and/or a direction normal to a tangent surface of the electrode contact most proximate to the seal and/or at the center of the surface of the electrode contact (longitudinal and/or lateral direction) and/or a direction normal to a tangent surface of the underlying carrier most proximate to the topmost surface of the seal, is about 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, or 0.3 mm, or any value or range of values therebetween in 0.001 mm increments (e.g., 0.085 to 0.222 mm, 0.123 mm, etc.).

FIG. 8B depicts an alternate embodiment where the electrode 148 is recessed in the carrier 149. Thus, there is a space 888 established by an extrapolated outer profile of the carrier 149 and the electrode surface of the electrode contact 148, and the sidewalls of the carrier 149. Briefly, in an exemplary embodiment, the height of the space 888 would be added to at least some of the aforementioned dimensions in the paragraph immediately precedent. As can be seen in the FIG. 8B, the material of the carrier 149 does not compress relative to the compression of the seal 670.

It is briefly noted that the structure of the carrier 149 that forms the recess/space 888 is not a seal, even if such might occur, in the absence of the seal 670, in some instances in an electrode array that does not utilize the seals disclosed herein and/or variations thereof. That is, the seal is a specific structure that is delta to the overall structure of the electrode array/carrier (even if the seal is monolithic with the carrier). One way of evaluating the structure in a nonfunctional manner is that the seal is a structure that extends above the outer profile of the carrier, in embodiments where the seal is a separate distinct component from the carrier. Another way of evaluating the structure in a nonfunctional manner is that the seal is a structure that extends above an extrapolated general outer profile of the carrier. That is, in an exemplary embodiment, the carrier will have a general shape, and the seals will be aberrations to that general shape.

Figure 9A:
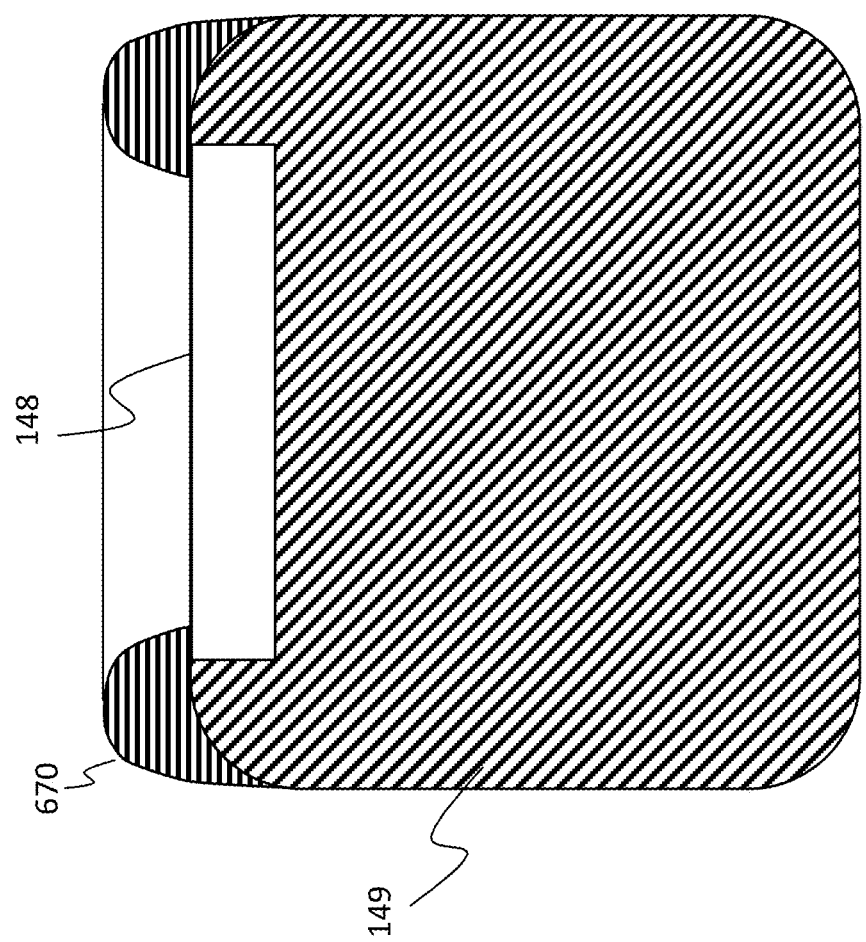

FIG. 9A depicts an exemplary embodiment where the seal 670 encroaches over the top surface of the electrode contact 148. In this regard, in at least some exemplary embodiments, the top of the electrode array may not have sufficient space for the seal to completely avoid contact with the electrode contact. Thus, in some embodiments, the seal 670 is interposed over a portion of the contact 148. Note that while the embodiment depicted in FIG. 9 is such that the seal 670 is in direct contact with the electrode 148, in some alternate embodiments, a portion of the carrier 149 is interposed between the seal 670 and the contact 148. In an exemplary embodiment, the seal 670 does not contact the contact 148 even though the seal 670, or more accurately, a portion thereof, is located above the contact.

FIG. 9B depicts an alternate embodiment where the seal 670 is not uniform with respect to location about the contact 148. More specifically, seal 670 of this embodiment has a height that varies, where the height becomes greater, relative to any of the aforementioned reference points the closer the seal is located to the center vertical plane of the electrode array (relative to FIG. 9B). In an exemplary embodiment, this can have utilitarian value with respect to accommodating the curvature of the modiolus wall. That said, in an alternate embodiment, the top surface of the seal is curved, relative to the frame of reference of FIG. 9B, but the height of the seal, relative to any of the aforementioned reference points, does not increase or otherwise vary, and in some embodiments, the height of the seal, again relative to any of the aforementioned reference points, decreases with location closer to the center vertical plane of the electrode array. In an exemplary embodiment, this can be the case with respect to a carrier that has a circular or an elliptical cross-section, etc. In this exemplary embodiment, the profile of the top surface can correspond to that of FIG. 9B.

Figure 9C:
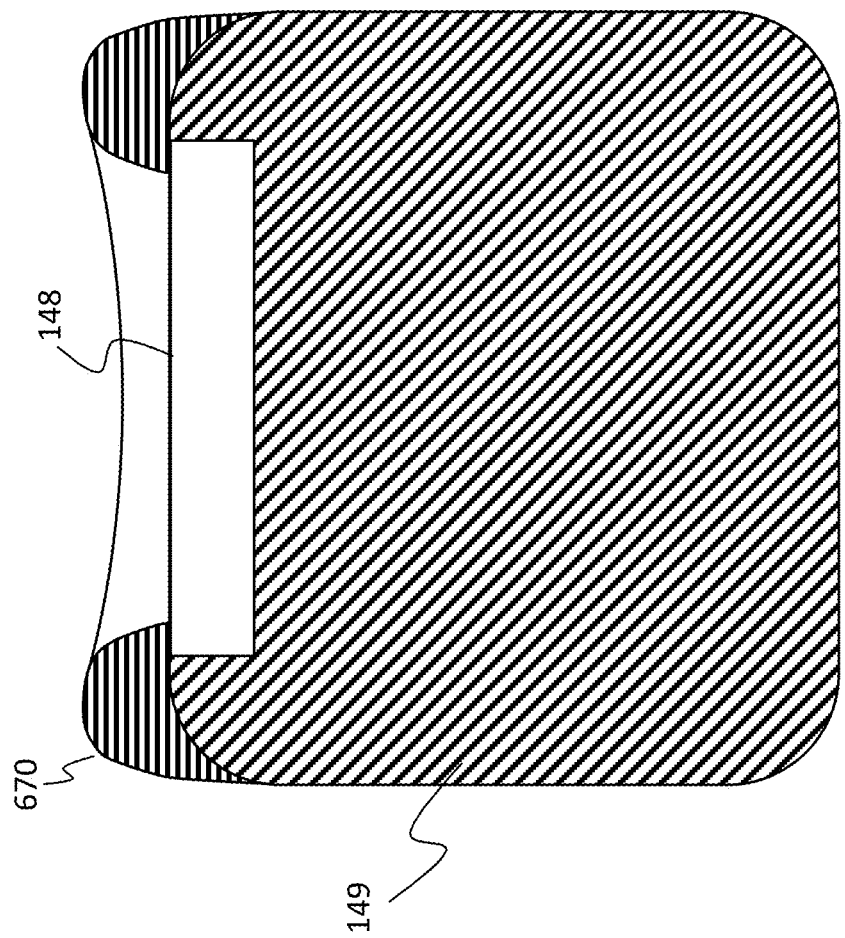

Still with reference to FIG. 9B, it can be seen that reference lines 901 and 902 have been interposed over the schematic. These lines all extend through the longitudinal axis 201 of the electrode array. In an exemplary embodiment, the top surface of the seal can be measured as a distance from line 901 in a direction parallel to line 902. In an exemplary embodiment, in a relaxed state (and the aforementioned values are relative to the relaxed state, when the electrode array is held straight away from contact with another structure and the seals, and/or when the electrode array is permitted to curl but still there is no contact with another structure in the seals), the height of the seal as measured from line 901 in a direction parallel to line 902 increases with location closer to line 902. In another embodiment, the height of the seal as measured from line 901 in a direction parallel to line 902 remains the same with location closer to line 902. That said, in an alternate embodiment, the height of the seal as measured from line 901 in a direction parallel to line 902 decreases with location closer to line 902. In this vein, FIG. 9C depicts another exemplary embodiment where the curvature of the top surface of the seal is convex relative to the longitudinal axis of the electrode array. In an exemplary embodiment, this can have utilitarian value with respect to achieving a regular/even distribution of the compression of the seal even though the curvature of the modiolus wall is such that distance from a local portion of the modiolus wall and the longitudinal axis of the electrode array is smallest at the center plane of the electrode array, at least when utilizing a non-rectangular cross-section carrier (and, in some embodiments, the opposite is the case with respect to the utilization of a rectangular cross-section carrier, and hence the embodiment of FIG. 9B). It is noted that for purposes of convenience a rectangular cross-section carrier is utilized in FIG. 9C. It will be understood how the features of FIG. 9C can be applied to an electric carrier having a curved cross-section.

Figure 10:
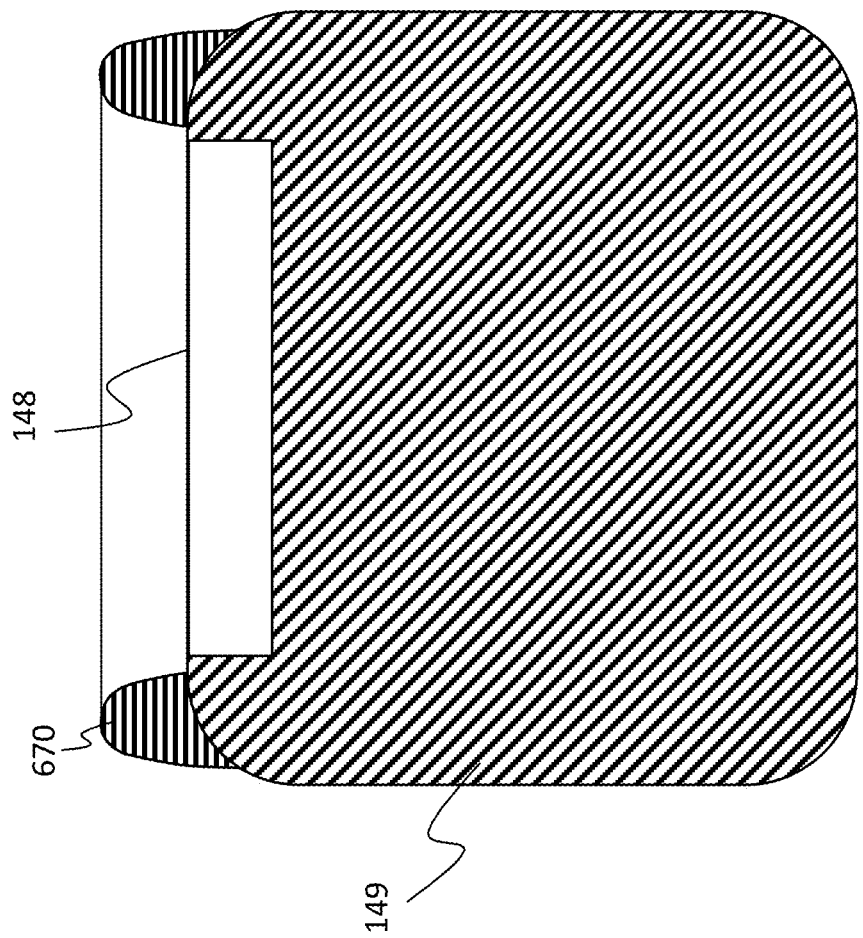
Figure 11:
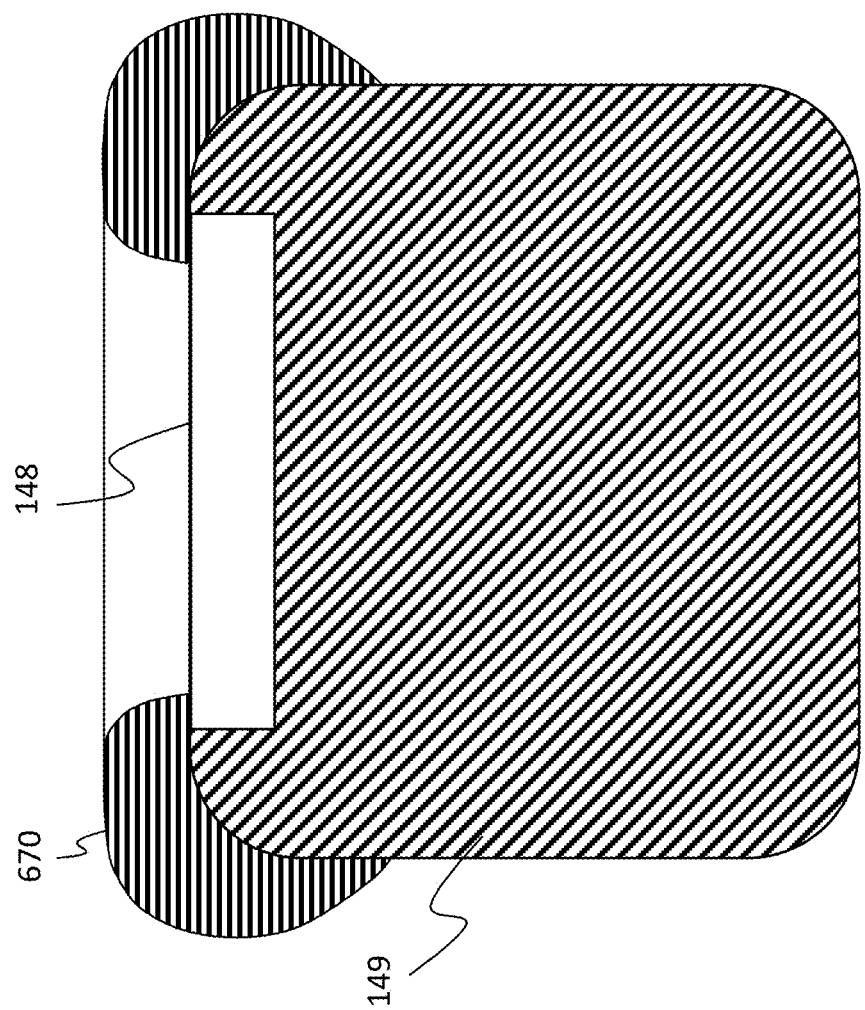

The embodiments detailed above have been directed to a structure of the seal 670 where the outer profile of the seal is flush with the outermost profile of the carrier 149 in the horizontal direction. FIG. 10 depicts an alternate embodiment where the outermost profile of the seal is inboard of the outermost profile of the carrier 149 in the horizontal direction. Conversely, FIG. 11 depicts an exemplary embodiment of an alternate embodiment where the outermost profile of the seal is outboard of the outermost profile the carrier 149 in the horizontal direction. Note that these are in the relaxed states.

In some exemplary embodiments, the electrode contacts are curved to at least approximately match the curve of the modiolus wall. It is noted that in at least some exemplary embodiments, the electrode contacts utilized are noncompliant electrode contacts in that the electrode contacts substantially maintain their form after insertion into the cochlea. That said, in some alternate embodiments, the contacts are compliant. In some exemplary embodiments, the electrode contacts are made of relatively hard platinum material, and the electrode contacts are relatively inflexible.

Figure 12:
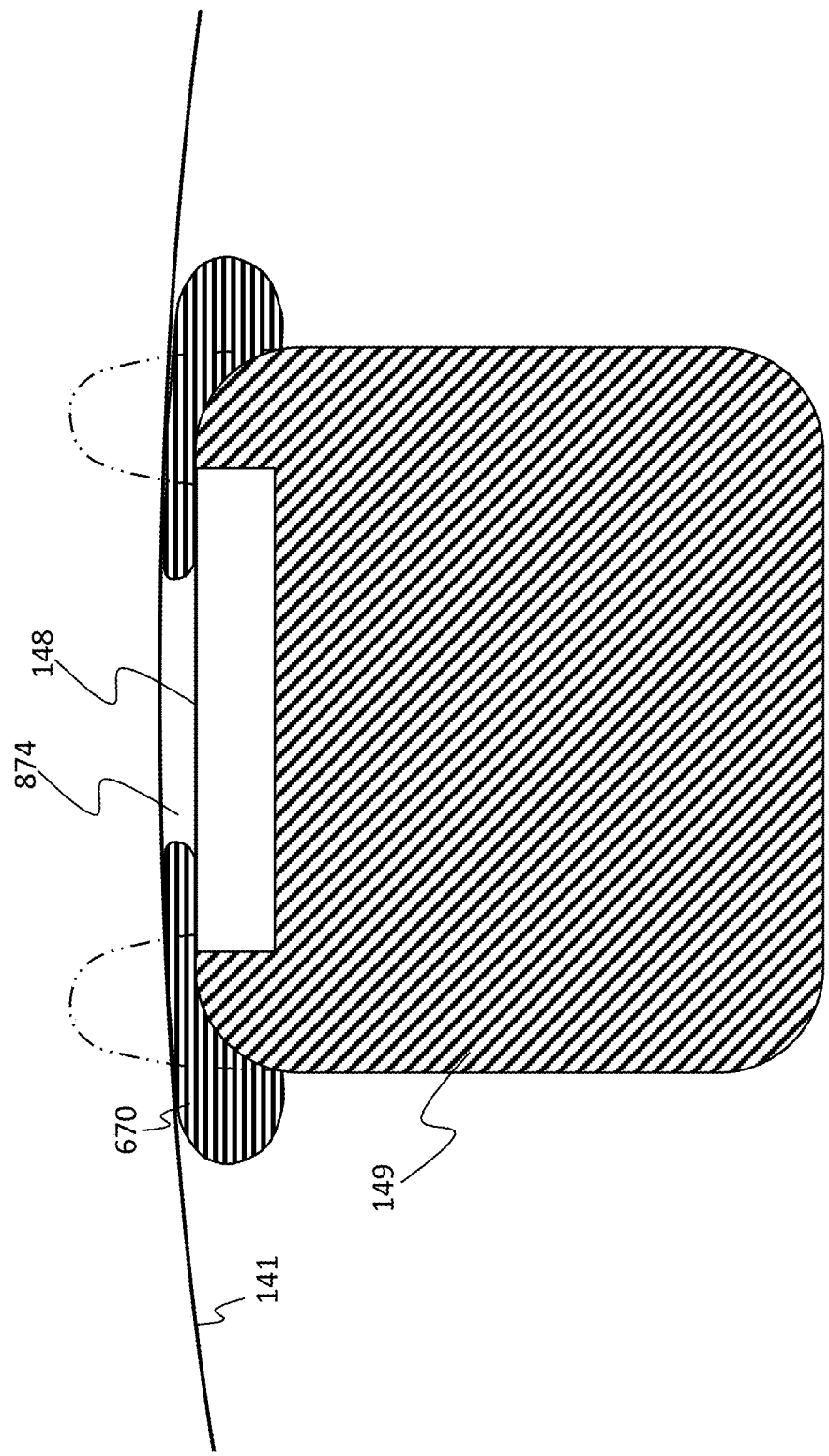

While the embodiment of FIG. 8B depicted compression that is relatively minor relative to the relaxed state of the seal, FIG. 12 depicts a more aggressive level of compression of the seal when the electrode array is finally located in the cochlea. Interposed on the schematic and phantom lines is the cross-sectional view of the relaxed seal. As can be seen, in an exemplary embodiment, the compression can compress the seal such that a significant amount of the top surface of the contact 148 is covered by the now compressed seal relative to that which was the case when the seal was in its relaxed state. Any amount of encroachment by the seal on to the surface or above the surface of the contact 148 is acceptable providing that there is sufficient unobstructed contact surface for the electrode array to operate in a utilitarian manner.

Figure 13:
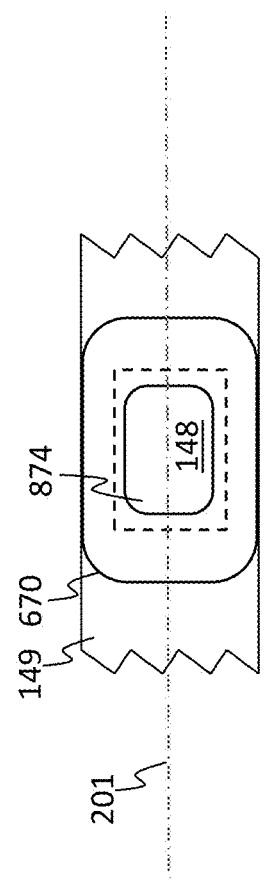
FIGS. 13-17 are exemplary top views of some exemplary portions of some exemplary cochlear electrode arrays according to some exemplary embodiments.

FIG. 13 depicts a top view of the seal 670 as compressed in a manner akin to that of FIG. 12. As can be seen, the seal 670 encroaches over the contact 148 (the outlines of which are depicted in dashed lines because of such) over all of the outer edges of the contact 148. This has the effect of reducing the volume 874 that is established between the modiolus wall (not shown), the seal, and the contact (and any portions of the carrier that may also establish the boundaries of that volume) relative to that which would be the case with respect to less compression, in at least some exemplary embodiments (because the seal extends inward towards the center of the top surface of the contact 148).

It is briefly noted that in an exemplary embodiment, the distance between the topmost portion of the seal and line 901 as measured parallel to line 902 and/or the average distance (mean or median) between the topmost portions in their entirety of the seal and line 901 as measured parallel to line 902 is decreased by equal to or more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 32%, 34%, 36%, 38%, or 40% or more, or any value or range of values therebetween in 0.1% increments owing to the compression after the electrode array is fully and completely and finally inserted into the cochlea such that it is fully against the modiolus wall relative to that which is the case in the relaxed state. In an exemplary embodiment, at least 99.5%, 99%, 98.5%, 98%, 97.5%, 97%, 96.5%, 96%, 95.5%, 95%, 94%, 93%, 92%, 91%, 90%, 89%, 88%, 87%, 86%, 85%, 84%, 83%, 82%, 81%, 80%, 79%, 78%, 77%, 76%, or 75%, or any value or range of values therebetween in 0.1% increments is due to the compression of the seal (as opposed to compression of the carrier).

It is briefly noted that in an exemplary embodiment, the shortest distance between the topmost portion of the seal and the tangent surface of the underlying carrier surface (or extrapolated surface in the case of a monolithic design) is decreased by equal to or more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 32%, 34%, 36%, 38%, 40%, 45%, 50%, 55%, 60%, 65%, 70%, 75%, 80%, 85%, 90% or 95% or more or any value or range of values therebetween in 0.1% increments owing to the compression after the electrode array is fully and completely and finally inserted into the cochlea such that it is fully against the modiolus wall relative to that which is the case in the relaxed state. Note that in some embodiments, a completely uncompressed barrier can have utilitarian value. If the surface of the barrier was just touching the wall, creating a barrier, such can be utilized in some embodiments.

Figure 14:
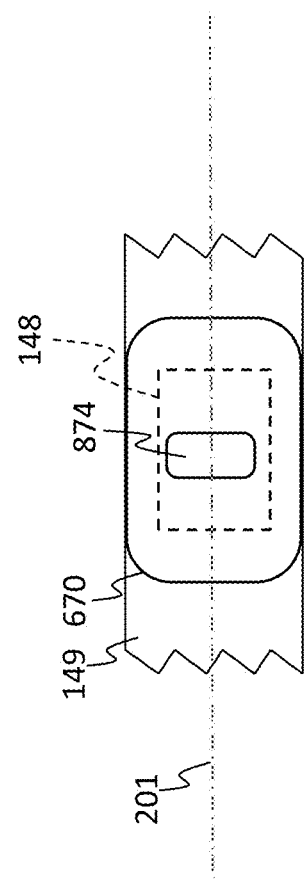
Figure 15:
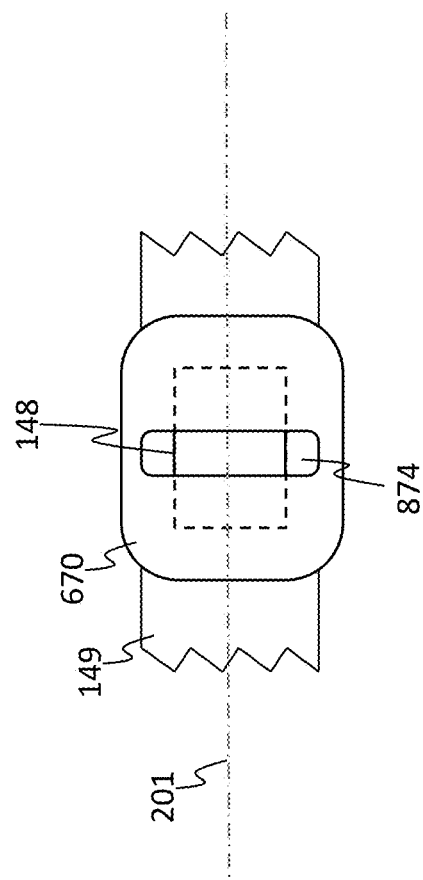

FIG. 14 depicts another exemplary embodiment depicting deformation of the seal 670 when it is fully compressed. Here, it can be seen that the deformation of the seal is greater with respect to the portions thereof closer to the longitudinal axis relative to portions of the seal that are further away from the longitudinal axis. This is not only due to the fact that the seal is of a non-square or rectangular arrangement (in its relaxed state). In this regard, owing to the curvature of the modiolus wall, and depending on the geometry of the carrier, the compression forces will be greatest at the locations closer to the longitudinal axis. Thus, in an exemplary embodiment, the resulting volume 874 is a non-square or rectangular shape (or, in some other embodiments, an elliptical shape or the like), with the long axis normal to the longitudinal axis 201 (in the frame of reference of FIG. 14). This is the case even though the seal in the undeformed state had a uniform or at least generally uniform distance from the outer boundaries of the contact 148. FIG. 15 depicts a similar phenomenon but where the seal 670 expands outward away from the longitudinal axis 201 as well (and can also expand outward along the longitudinal axis 201. Here, it can be seen that the volume 874 is even more elongate than that of FIG. 14, and also that a portion of the boundary of volume 874 is established by the underlying carrier material 149.

Figure 16:
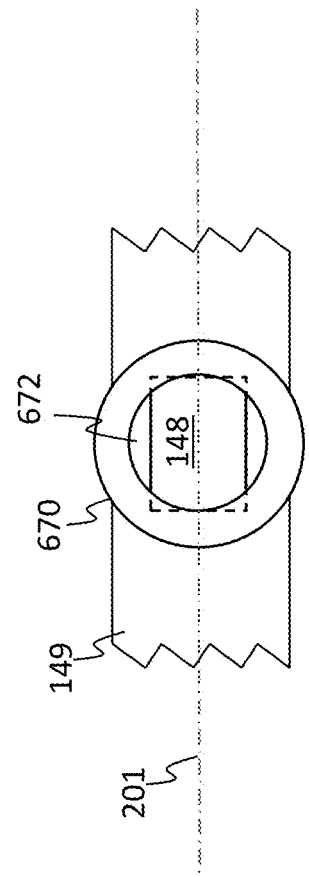
Figure 17:
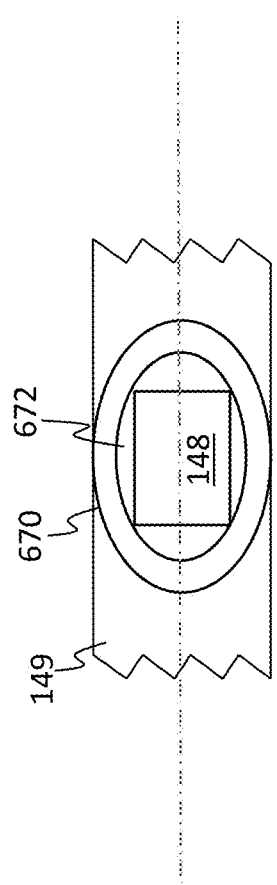

As noted above, some different shapes of the seal, when viewed from above, are circular. In this regard, FIG. 16 depicts an exemplary seal 670 in the undeformed/relaxed state. As can be seen, a portion of contact 148 is covered by the seal. Also as can be seen, a portion of the carrier 149 adjacent the contact 148 is not covered by the seal. Accordingly, space 672 (or the bowl) is established by the carrier material 149, the surface of the contact 148, and the seal 672. FIG. 17 depicts an elliptical seal 670 in its undeformed state when viewed from above. Again, any arrangement of seals that can have utilitarian value can be utilized in at least some exemplary embodiments.

It is noted that in at least some exemplary embodiments, the seals detailed herein add to the normal cross-sectional dimensions of the electrode array. It is this addition that is compressed/deformed so as to establish the seals against the modiolus wall, as opposed to the material of the carrier.

In view of the above, in an exemplary embodiment, there is an implantable stimulating assembly, such as by way of example only and not by way of limitation, the electrode assembly 145, wherein the electrode assembly includes an electrode contact (e.g., a contact such as element 148 above), and an electrode carrier member (e.g., carrier 148 detailed above). In some other embodiments, the electrode assembly can be that of a pacemaker or other medical device. The teachings detailed herein can be applicable to any stimulating assembly that utilizes a contact providing that the art enables such. In an exemplary embodiment, there is a barrier extending about the electrode contact located on the outside of the carrier member. This barrier can be the gel-like seals detailed above, or foam seals, etc. Note also that in at least some exemplary embodiments, a seal need not necessarily be established. That is, a barrier need not be a seal. Note also that the teachings detailed herein can be applicable to application to fewer than all of the electrodes of the electrode array of the electrode assembly 145. By way of example only and not by way of limitation, every other electrode could have a barrier extending about the electrode contact outside of the carrier member. Every third electrode could have such barrier, every fourth electrode, etc. Alternatively, in an exemplary embodiment, every two electrodes could have such barriers, and then every two electrodes would not have such barriers and so on. Alternatively, in an exemplary embodiment, every two electrodes could have such barriers, and then every one electrode would not have such barriers, and so on. Any arrangement utilizing barriers that can have utilitarian value can be utilized in at least some exemplary embodiments. Note also that in at least some exemplary embodiments, a given barrier can encompass two or more electrodes. That is, a barrier may separate electrodes from other electrodes but not all electrodes from all electrodes. By way of example only and not by way of limitation, there can be a barrier, such as a seal, that encompasses two or three or more electrodes. Another barrier could be located proximate that barrier that encompasses two or three or more electrodes, etc. Such could be utilized in a case where current spreading is not as much of a concern, on a per unit length of the modiolus wall, as in other locations, or even overall. That is, in some exemplary embodiments, there can be utilitarian value with respect to limiting current spread beyond a certain range, but permitting such within a range that would encompass a footprint that would encompass two or three or more electrodes. Accordingly, as shown in FIG. 7, the cochlear electrode array includes respective electrode contacts having respective surfaces 67184 facing outwards towards an outside of the cochlear electrode array that are located below crests 677212 of the respective barriers surrounding the respective electrode contacts.

In an exemplary embodiment, the barrier can be a continuous lip on the carrier member, concomitant with the teachings detailed above. In an exemplary embodiment, the barrier is a separate component from the carrier. In an exemplary embodiment, the barrier is placed onto the carrier after the carrier is cured. That said, in an alternate embodiment, the barrier is added to the carrier during the curing process. Moreover, it is noted that while the embodiments detailed above depict a generally defined and uniform demarcation surface between the barrier and the carrier, in alternative embodiment, the demarcation surface can be complex. For example, a portion of the carrier could envelop a base portion of the barrier. Note also that in an exemplary embodiment, another component can be utilized to ensure that the barrier is retained to the carrier. By way of example only and not by way of limitation, a plastic "rivet" or the like can extend from inside the barrier to inside the carrier, and the materials of those two components can be formed there around, such that the load bearing surfaces of the rivet (the widened portions at the ends of the rivet) are enveloped by the material of the barrier and the carrier, with the shank of the rivet connecting the barrier and the carrier together, the shank extending from the barrier to the carrier.

In view of various figures above, it can be understood that the outer surface of the barrier and the electrode contact collectively form a crater on the carrier member, in that a crater has a rim surrounding a somewhat even surfaced portion. It is noted that by even surfaced portion, this does not mean that the surface is flat. Indeed, in an exemplary embodiment, where the electrode contact is a half band electrode, the even surface will be curved. Still, consistent with a scenario where a crater is large enough, the curvature of the surface of the moon, for example, can be both smooth and curved. It is noted by the phrase "collectively form," this does not exclude other portions that form the crater. By way of example only and not by way of limitation, with respect to the embodiment in FIG. 7A above, it is to be understood that a portion of the carrier 149 forms that even surface, or, in the case of a recessed electrode, that carrier 149 forms the portion of the sidewalls of the crater, albeit perhaps a staggered fashion.

Consistent with the teachings detailed above, the barrier can be one of a curved barrier (circular, elliptical/oval, eccentric, etc.) or a rectangular barrier (square or non-square) when viewed from the top.

In an exemplary embodiment, the barrier is configured to be urged against tissue of a recipient, such as by way of example only and not by way of limitation, the modiolus wall of the cochlea (although in other embodiments, the tissue is the tissue of the lateral wall—more on this below, or another wall the cochlea—indeed, in some embodiments, it is the wall of the scala vestibuli instead of or in addition to the wall of the scala timpani (in the case of a dual electrode array) to which the barrier abuts), such that the barrier, the surface of the electrode contact, and optionally, the carrier of the electrode contact form a closed volume (e.g., volume 874). Thus, in an exemplary embodiment, the barrier is configured to be urged against tissue of the recipient such that at least three of the tissue, the barrier, the electrode contact or the carrier form a closed volume, wherein the at least three include the tissue, the barrier and the electrode contact. In this exemplary embodiment, the barrier is configured to inhibit a flow of body fluids from outside the barrier to inside the barrier when the barrier is urged against the tissue. Consistent with the teachings directed towards utilization of the barriers detailed herein with respect to a cochlear implant, the tissue can be the inside of a cochlea, and the fluid can be perilymph.

Some embodiments directed towards the cochlear electrode array will now be described in greater detail. In an exemplary embodiment, there is a cochlear electrode array, such as the electrode arrays detailed above and variations thereof, comprising an array of electrode contacts, these contacts can be flat/planar contacts or can be so-called half band contracts. Note also that other types of contacts can be used, such as curved contacts, bent contacts, ball contacts, cylindrical contacts, etc. Any type of electrode contact the utilized with the teachings detailed herein can be utilized in at least some exemplary embodiments. Note also that this is the case with respect to embodiments where the electrodes are not arranged in an array, but instead are arranged in a different manner and/or assemblies that utilize only one electrode (at least one positive electrode—most embodiments will utilize a return electrode as well). Again, there is a carrier that carries the array of electrode contacts. In an exemplary embodiment, this carrier can be made of silicone configured for implantation into a cochlea of a recipient. Again, the respective barriers surround the electrode contacts in accordance with the teachings detailed herein and/or variations thereof. In an exemplary embodiment, these barriers can be seals.

In some respects, in at least some exemplary embodiments, the cochlear electrode array resembles a tentacle of an octopus. This is most imminently the case with respect to a tapered electrode, but can also be the case with respect to a non-tapered electrode. This is most imminently the case with respect to barriers that have a curved shape, especially a circular shape, when viewed from the top. That said, even a rectangular barrier can still give the resemblance of the suction cup of an octopus.

The feature of a suction cup can be applicable in at least some exemplary embodiments. To be clear, in an exemplary embodiment, the barrier forms essentially a cup, or, alternatively, a bowl (or crater, as noted above), with the barrier, the electrode contacts, and, in some instances, the electrode carrier, forming the interior surfaces of the cup/bowl. Moreover, in at least some exemplary embodiments, the cup formed by the seal is such that when the seal is compressed by a certain amount, a suction could be created, in some embodiments, such that the suction effect further adheres the electrode array against the modiolus wall of the cochlea. This suction effect can be such that the pressure inside the bowl/cup is less than that outside the bowl/cup, and work in a manner analogous to a familiar suction cup that one might apply to a window or the like, where the elastic tendencies of the components that form the seal push outward away from the surface, but the pressure inside the cup is lower than that outside, thus maintaining the suction cup against the surface. Accordingly, in an exemplary embodiment, the electrode array can be configured such that during insertion and during a temporal period immediately proximate thereto, the mechanical properties of the electrode array impart greater forces that drive the array closer to the modiolus wall than that which is the case at a later temporal period. This initial higher force can result in the greater compression of the seal, and can be analogous to the initial force applied to a suction cup against a surface. Later, the mechanical forces in the electrode array can be reduced, at least slightly, so that at least in part, the suction effect is created. By way of example only and not by way of limitation, an elastic stylet can be located inside the electrode array, which stylet drives the electrode array closer to the modiolus wall than that which is the case upon its removal. The stylet is maintained in the electrode array during the insertion process, and then, after the stylet has driven the electrode array closer to the modiolus wall and compressed the seals to the maximum, the stylet is removed, thus relaxing the mechanical forces of the electrode array driving the electrode array towards the modiolus wall. The electrode array then moves away from the modiolus wall, at least slightly, thus creating the aforementioned suction effect. Any arrangement of changing the mechanical forces of the electrode array that can drive the electrode array to the modiolus wall can be utilized in at least some exemplary embodiments.

In an exemplary embodiment, the aforementioned barriers prevent the electrode contacts from contacting the cochlea, at least some of the contacts. In this regard, in an exemplary embodiment, the barriers maintain an offset between the electrode contacts and the modiolus wall of the cochlea. Note further that in an exemplary embodiment, the barriers prevent the carrier of the electrode array from contacting the modiolus wall, or, in some embodiments, any other wall of the cochlea (save for the location where the electrode array enters the cochlea, at least in some embodiments). In this regard, in an exemplary embodiment, the electrode array is configured such that of the components of the electrode array, only the barriers contact the modiolus wall of the cochlea when fully inserted into the cochlea.

The prevention of the contact of the electrode contacts with the modiolus wall is achieved, in some embodiments, entirely due to the barriers, while in other embodiments, is it the combination of the barrier and the carrier (e.g., in the case where the electrode contacts are recessed) that prevents the contacts of the electrode contacts with the modiolus wall.

In an exemplary embodiment, subsequent implantation, after the electrode array has achieved a steady-state (note that in at least some of the embodiments, all of the teachings detailed herein are applicable to this steady-state arrangement unless otherwise noted), the barriers maintain a distance between the electrode contacts in the modiolus wall of at least 0.01 mm, 0.02 mm, 0.03 mm, 0.04 mm, 0.05 mm, 0.06 mm, 0.07 mm, 0.08 mm, 0.09 mm, 0.10 mm, 0.11 mm, 0.12 mm, 0.13 mm, 0.14 mm, 0.15 mm, 0.16 mm, 0.17 mm, 0.18 mm, 0.19 mm, 0.20 mm, 0.21 mm, 0.22 mm, 0.23 mm, 0.24 mm, 0.25 mm, 0.26 mm, 0.27 mm, 0.28 mm, 0.29 mm, 0.3 mm, 0.31 mm, 0.32 mm, 0.33 mm, 0.34 mm, 0.35 mm, 0.36 mm, 0.37 mm, 0.38 mm, 0.39 mm, 0.40 mm, 0.45 mm, 0.5 mm, 0.55 mm, 0.6 mm, 0.7 mm, 0.8 mm, 0.9 mm, or more or any value, or range of values therebetween in 0.005 mm increments. It is noted that in some embodiments, the aforementioned distances are due entirely to the barriers, while in other embodiments, the aforementioned distances or do in view of the combination of the barrier and the carrier, such as in the case of a recessed electrode. Still further, in an exemplary embodiment, the aforementioned values are the differences between that which would exist (the delta) in the absence of the barrier (e.g., if only the carrier member were present—no barrier was present).

Consistent with the teachings detailed above, in an exemplary embodiment, the barriers are configured to be squished against a wall of the cochlea so that the barriers form seals between the respective electrode contacts and the ambient environment (i.e., the environment within the cochlea). In an exemplary embodiment, the material of the barriers is squishy, while the material of the carrier of the electrode array is not squishy, or at least effectively less squishy, and, in some instances, substantially less squishy, than the carrier. Another way of saying this is that in an exemplary embodiment, the barrier is relatively squishy compared to the carrier of the electrode contacts.

In an exemplary embodiment, the carrier has a first durometer value (at least those portions proximate the barrier) and the barrier has a second durometer value that is substantially lower than the first barometer value. In an exemplary embodiment, the carrier is made of a silicon having a durometer value of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 type A, or any value or range of values therebetween in increments of 1 (e.g., 30-60, etc.). Conversely, in an exemplary embodiment, the barrier can be made of a liquid silicon rubber, such as by way of example only and not by way of limitation, MED-4801, manufactured by NuSil Silicone Technology in Carpinteria, Calif., USA. In an exemplary embodiment, the following can be applicable to the material of the barrier:

| Typical Properties | Result | Metric Conv. | ASTM | NT-TM |
|---|---|---|---|---|
| Uncured: | | | | |
| Appearance | Translucent | — | D9020 | 002 |
| Extrusion Rate* | 160 gpm | — | — | 033 |
| Work Time | 6 hours minimum | — | — | 008 |
| Cured: 5 minutes @ 150° C. (302° F.) | | | | |
| Durometer, Type 00 | 40 | — | D2240 | 006 |
| Tensile Strength | 325 psi | 2.2 MPa | D412, D882 | 007 |
| Elongation | 1,075% | — | D412, D882 | 007 |
| Tear Strength | 60 ppi | 10.6 kN/m | D624 | 009 |
| Stress @ 100% Strain | 10 psi | 0.1 MPa | D412, D882 | 007 |
| Stress @ 300% Strain | 30 psi | 0.2 MPa | D412, D882 | 007 |
| Stress @ 500% Strain | 65 psi | 0.4 MPa | D412, D882 | 007 |

*Performed using a SEMCO ® 440 nozzle with a ⅛" orifice and 90 +/− 5 psi air pressure In an exemplary embodiment, the barrier is made of a silicon having a durometer value of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 type 00, or any value or range of values therebetween in 1 increments (e.g., 30-60, etc.).

In an exemplary embodiment, the material of the barrier is that of a very low durometer material, and in some embodiments, an extremely low durometer material. In an exemplary embodiment, the barrier is that of a low durometer material relative to the material of the carrier, at least at locations of the carrier proximate the barrier, and in an exemplary embodiment, the barrier is that of a very low durometer material relative to the material of the carrier, again at least at the locations of the carrier proximate the barrier.

As noted above, in at least some exemplary embodiments, the electrode array is a perimodiolar electrode array. That said, in some alternate embodiments, the electrode array can be a lateral wall electrode array, where, essentially, the electrode contacts in the barriers are located on the opposite side of the electrode array, such that the contacts are positioned proximate the wall of the cochlea opposite the modiolus wall. Note also that in an exemplary embodiment, the electrode array can be a quasi-mid-scala electrode array. In such an exemplary embodiment. The seals, or more accurately, the height of the seals could be extended quite a bit relative to that detailed above. In at least some exemplary embodiments, the barriers would be a composite barrier, where a first portion of the barrier was made of a material having a first durometer value (e.g., that of the carrier, or even greater), or could be made of a plastic material or the like that has little to no compressibility, and a second portion of the barrier could be made by the squishy sealing materials detailed above, having a second durometer value lower than the first durometer value. In an exemplary embodiment, these barriers might be like smokestacks of a ship or the like, with the seal located at the top, and the base embedded in the carrier. Moreover, in an exemplary embodiment, a support structure can be utilized to provide some structural support to the distal ends of these barriers in scenarios where the barriers are relatively elongate relative to those depicted in the figures above. By way of example only and not by way of limitation, ribs could extend between the barriers, which ribs could be isolated from the carrier and/or which ribs could also extend to the carrier as well.

It is noted that in some exemplary embodiments, a viscoelastic material can be utilized for at least a portion of the seals detailed herein. In an exemplary embodiment, the material can be such that the seals, once compressed, retain at least a substantial portion of that compression for at least a number of seconds, if not minutes, after the initial compression. Such can have utilitarian value with respect to reducing the overall cross-section of the electrode array prior to insertion into the cochlea such that the whole into the cochlea can have a smaller diameter than that which would otherwise be the case in the absence of such compression. Alternatively, in an exemplary embodiment, the seals can be made of a material that swells after insertion into the cochlea, such as by way of example, a hydrogel type material. Any arrangement of the seals that can enable the teachings detailed herein and has utilitarian value can be utilized in at least some exemplary embodiments.

In some exemplary embodiments, the durometer of the seal is tuned with respect to location on the electrode array. First, it is noted that in at least some exemplary embodiments, the seals are not monolithic. A given seal can comprise a plurality of different components and need not necessarily be of the same material. Second, it is noted that in at least some exemplary embodiments, the compressibility characteristics of the seal can vary with location about the perimeter of the electrode contact. By way of example only and not by way of limitation, in an exemplary embodiment, the compressibility of the portions of the seal at the center plane through the longitudinal axis could be greater than that with respect to the portions of the seal that are away from the center plane in embodiments that utilize the curved carrier. Conversely, the opposite can be the case with respect to the embodiments that utilize the rectangular carrier. In some exemplary embodiments, the amounts of the seal material can vary as well. The heights can vary along the perimeter as detailed above. Any arrangement that can enable the teachings detailed herein and/or variations thereof can be utilized in at least some exemplary embodiments.

Figure 18:
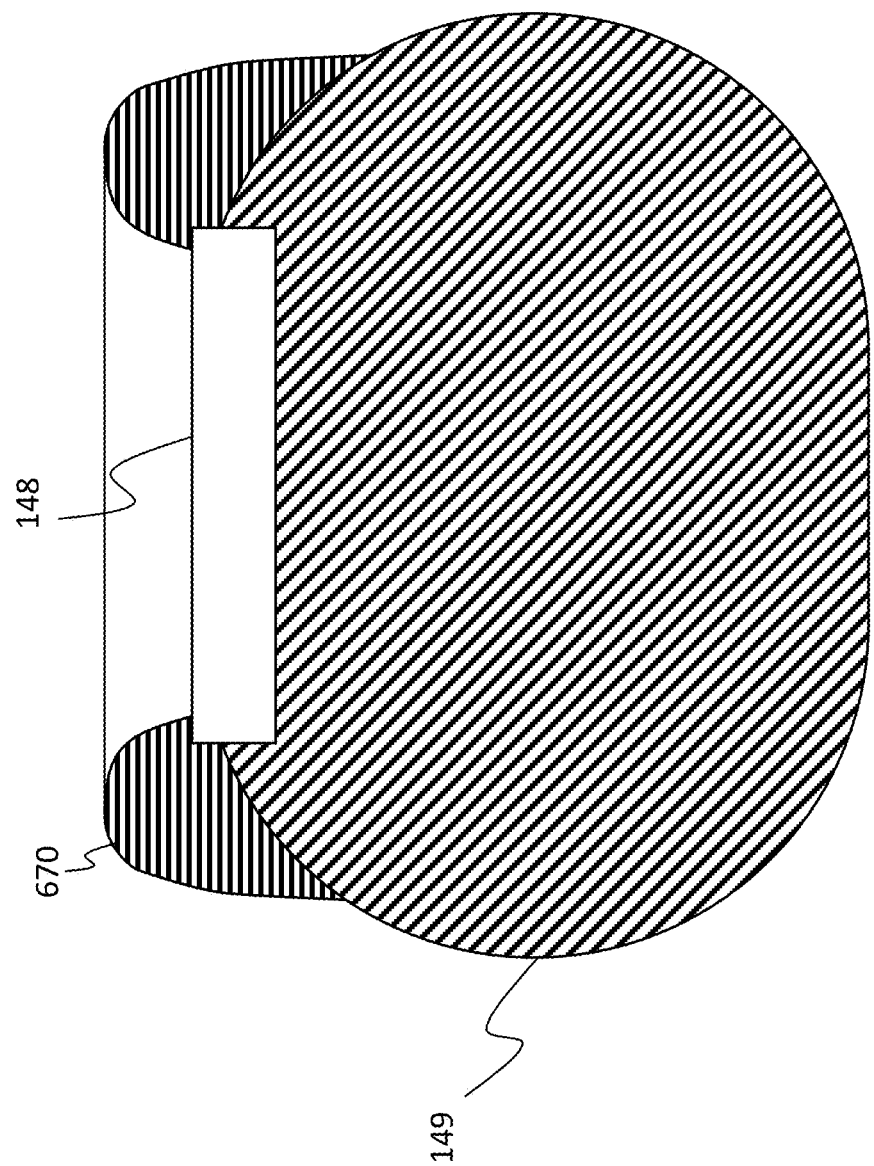
FIGS. 18-20 depict some exemplary cross-sections of some exemplary electrode arrays according to some exemplary embodiments.
Figure 19:
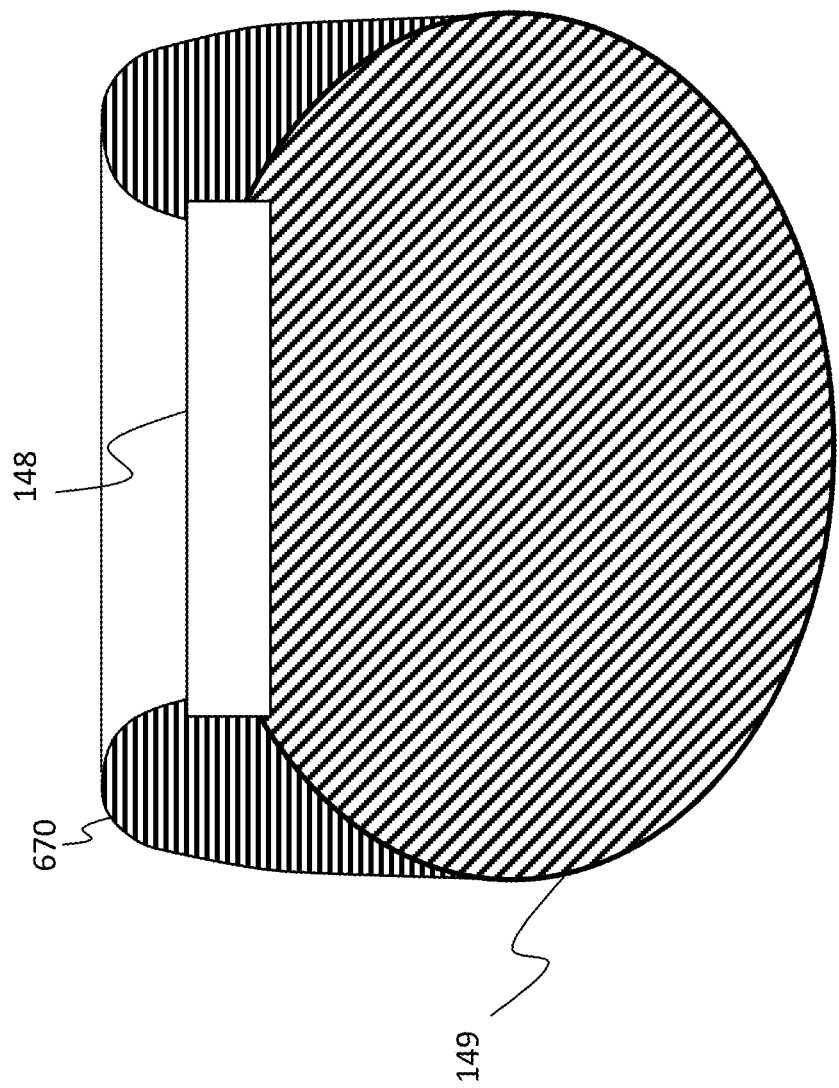
Figure 20:
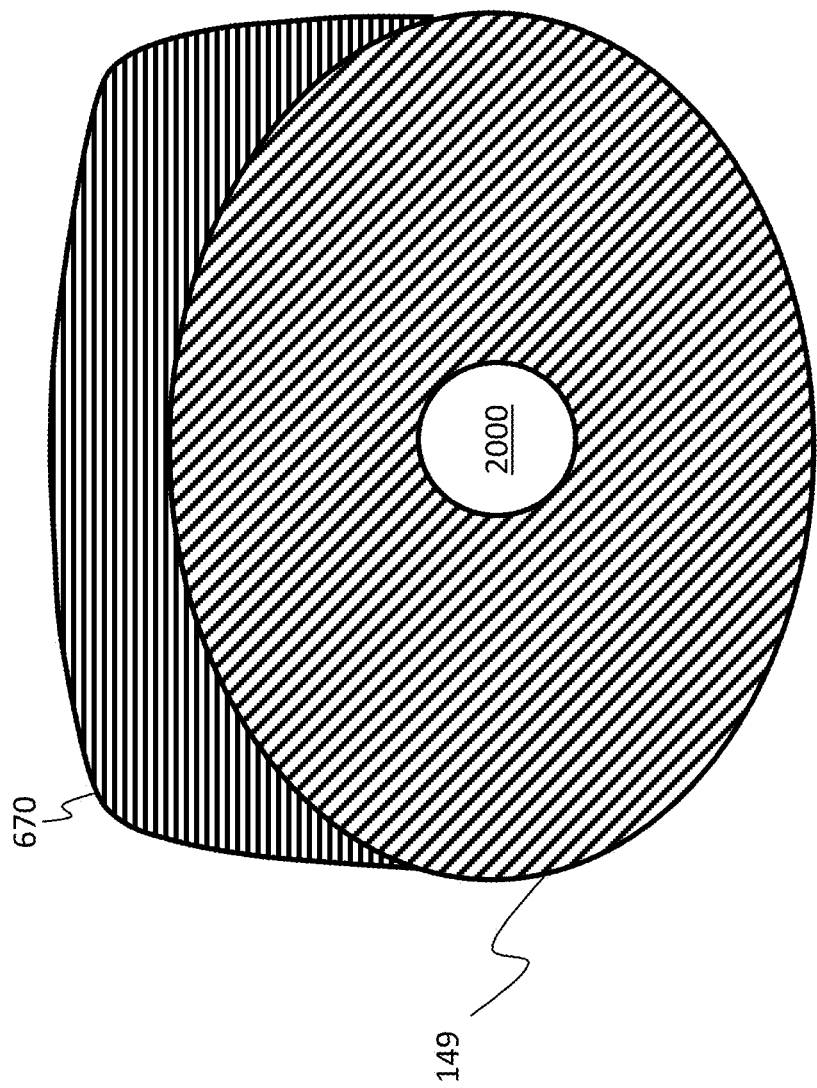

With reference to FIG. 18, in an exemplary embodiment, the carrier 149 has a generally curved outer cross-section lying on a plane normal to a longitudinal axis of the electrode array, and the barriers have a top surface that substantially lies in the same plane in a relaxed state. FIG. 19 depicts an alternate embodiment of such, where the electrode array has a generally curved outer cross-section (an oval shape, and thus a purely curved cross-section, but note also that in other embodiments, the carrier can be circular, etc.) lying on a plane normal to a longitudinal axis of the electrode array, and the barriers have a top surface that substantially lies in the same plane in a relaxed state. That said, in an alternate embodiment, the barriers have a top surface that substantially lies in an arcuate range. FIG. 20 depicts such an exemplary embodiment, where FIG. 20 depicts a section cut at a location before or after the electrode contact (e.g., where the seal has its lateral extension across the electrode array from one side of the electrode array to the other, as opposed to the location where the seal has its longitudinal extension, as in the cross-sections of FIGS. 18 and 19). As can be seen, in the exemplary embodiment, the barriers have a cross-section lying on a plane normal to the longitudinal axis that has a top surface that is curved in a relaxed state. Note also that the embodiments of FIGS. 18, 19, and 20 vis-à-vis the top surfaces of the seals can also be applicable to an electrode array having a carrier that is of the rectangular cross-section variety. With reference to FIG. 20, while FIG. 20 depicts a cross-section where the top surface of the seal is curved, in other embodiments, the top surface of the seal can be flat, concomitant with aforementioned embodiment where the barriers have a cross-section lying on a plane normal to the longitudinal axis that is a top surface that is substantially flat relaxed state and/or where the barriers have a top surface that substantially lies in the same plane in a relaxed state.

FIG. 20 also depicts an exemplary stiffening member/stylet 2000 according to the teachings detailed herein. By way of example only and not by way of limitation, in an exemplary embodiment, the stiffening member/stylet 2000 is made of Nitinol, or some other elastic and/or super elastic material. Any material that can have utilitarian value with respect to urging the electrode array against the modiolus wall (or the lateral wall in other embodiments) so as to enable the various barriers detailed herein to have utilitarian value can be utilized in at least some exemplary embodiments.

Again, while the embodiments of FIGS. 18 and 19 have been directed towards the utilization of a flat, planar electrode contact, in an exemplary embodiment, the electrode contact is a curved electrode contact, such as a half band electrode, which has a curved outer surface facing the modiolus wall. In an exemplary embodiment, the barriers detailed herein are also applicable to such electrode arrays having such contacts. In an exemplary embodiment, the barrier surrounds the electrode contacts such that a top surface of the barrier lies in the same plane, while in other embodiments, the barriers around the electrode contacts such that a top surface of the barrier lies in an arcuate space.

As noted above, in an exemplary embodiment, the electrode array is a pre-curved perimodiolar electrode array. In an exemplary embodiment, the barriers limit ingress and/or the egress of perilymph when the barriers are compressed against the modiolus wall. By "limit," it is meant that the ingress and/or egress of perilymph is frustrated in an effective manner relative to that which would be the case without the barrier. Note also that this includes the prevention of ingress and/or egress of perilymph. It is briefly noted that the modiolus wall is porous, and thus perilymph will be able to seep into and out of the volume 874 established by the electrode array with the seals and the modiolus wall. In this regard, perilymph "flows" within the cochlear ducts, but does not flow within the walls. Instead, perilymph seeps within the walls. Accordingly, in an exemplary embodiment, the teachings detailed herein form a volume partially bounded by the modiolus wall where perilymph is limited, including prevented, from flowing into and out of the volume, even though perilymph is not limited from seeping into and out of the volume, such seeping occurring through the modiolus wall.

Figure 21:
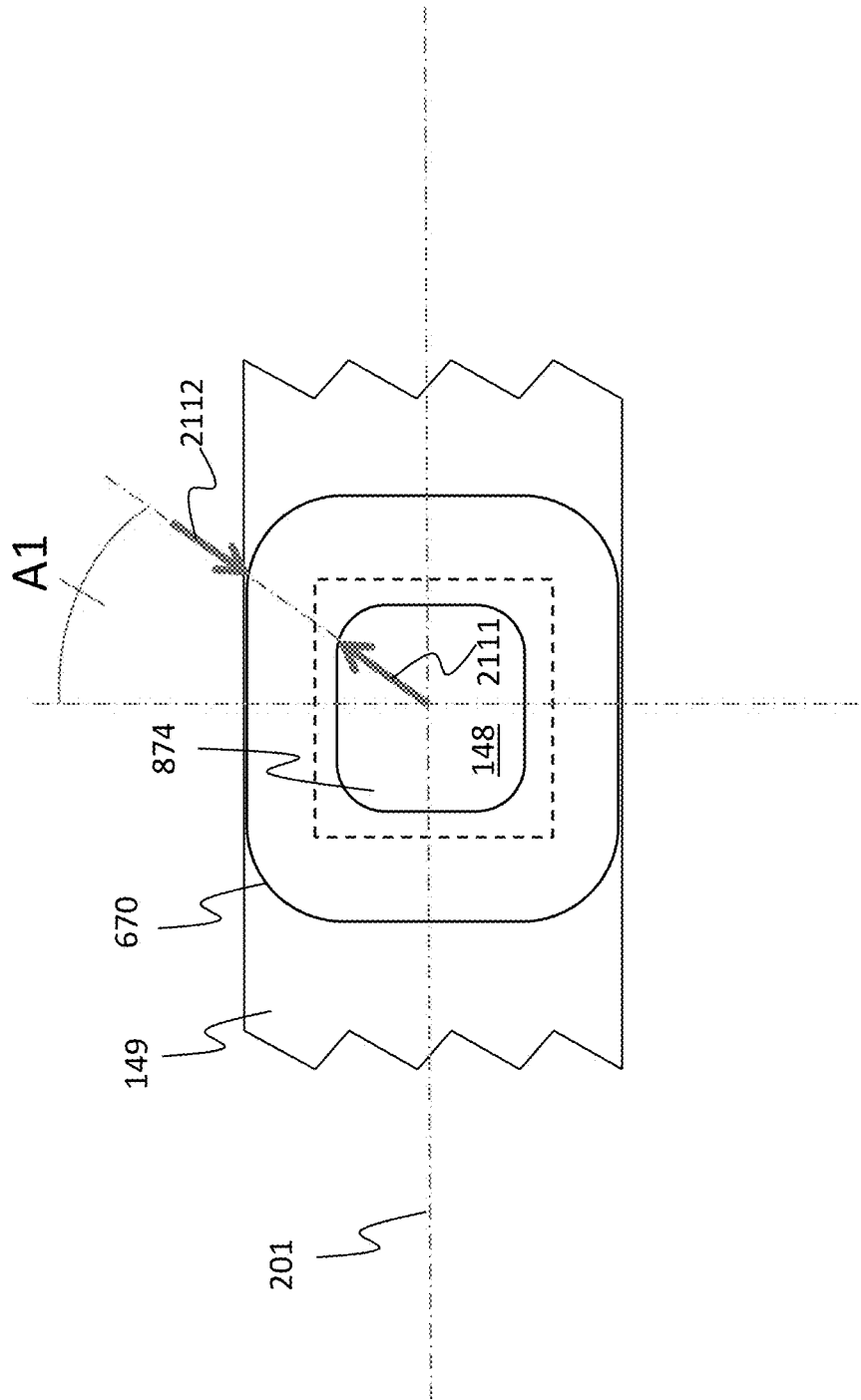
FIG. 21 depicts a top view of an electrode array according to an exemplary embodiment, upon which is superimposed some details associated with perilymph movement.

In an exemplary embodiment, the barriers detailed herein, such as those in the form of seals, are configured to limit the ingress and egress of perilymph one a plane that is parallel to a tangent surface of a given electrode contact at locations spanning 360°, which plane bisects the barrier. FIG. 21 depicts a conceptual drawling looking downward on a compressed barrier 670. Interposed thereon are two vectors, vector 2111 and vector 2112. These vectors represent, respectively, egress of perilymph from inside the volume 874, and ingress of perilymph from outside the volume 874. As can be seen, these vectors are depicted as lying on an axis that is at an angle A1 from an axis that is normal to the longitudinal axis 201 of the electrode array. In an exemplary embodiment, the barrier 670 is configured to limit ingress and egress, including completely prevent ingress and egress, over every angle A1 from 0 to 360 degrees.

Figure 22:
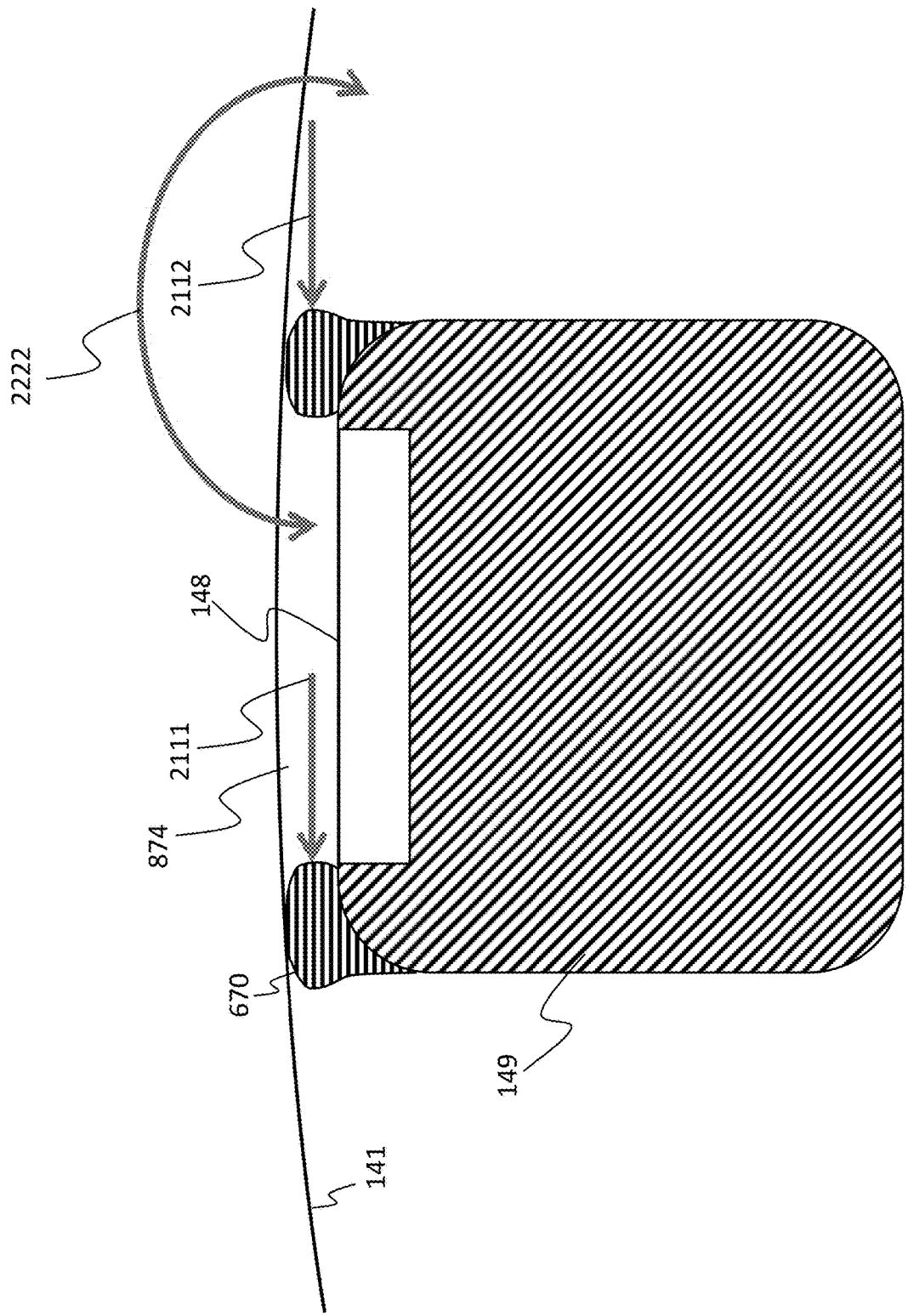
FIG. 22 depicts a cross-sectional view of a cochlear electrode array according to an exemplary embodiment along with a portion of a cochlea wall, upon which is superimposed some details associated with perilymph movement.

FIG. 22 depicts a side view of the phenomenon depicted in FIG. 21. As can be seen, the barrier 670 is limiting (in this embodiment, preventing) the egress of perilymph, represented by vector 2111, and preventing the ingress of perilymph, represented by vector 2112, on the plane parallel to the tangent surface of the electrode array 148. Also, as is conceptually depicted, is the seeping of the perilymph through the modiolus wall, which seeping is represented by element 2222. As can be seen, perilymph can seep both into volume 874 and out of volume 874 due to the porosity of the modiolus wall.

Note also that in at least some scenarios of use, perilymph will be able to seep between the surface of the barrier 670 and the surface of the modiolus wall 141. This seeping is akin to the seeping that can occur in any such seals. This is as opposed to perilymph flowing, which the barriers limit, and in some embodiments completely prevents.

Figure 23:
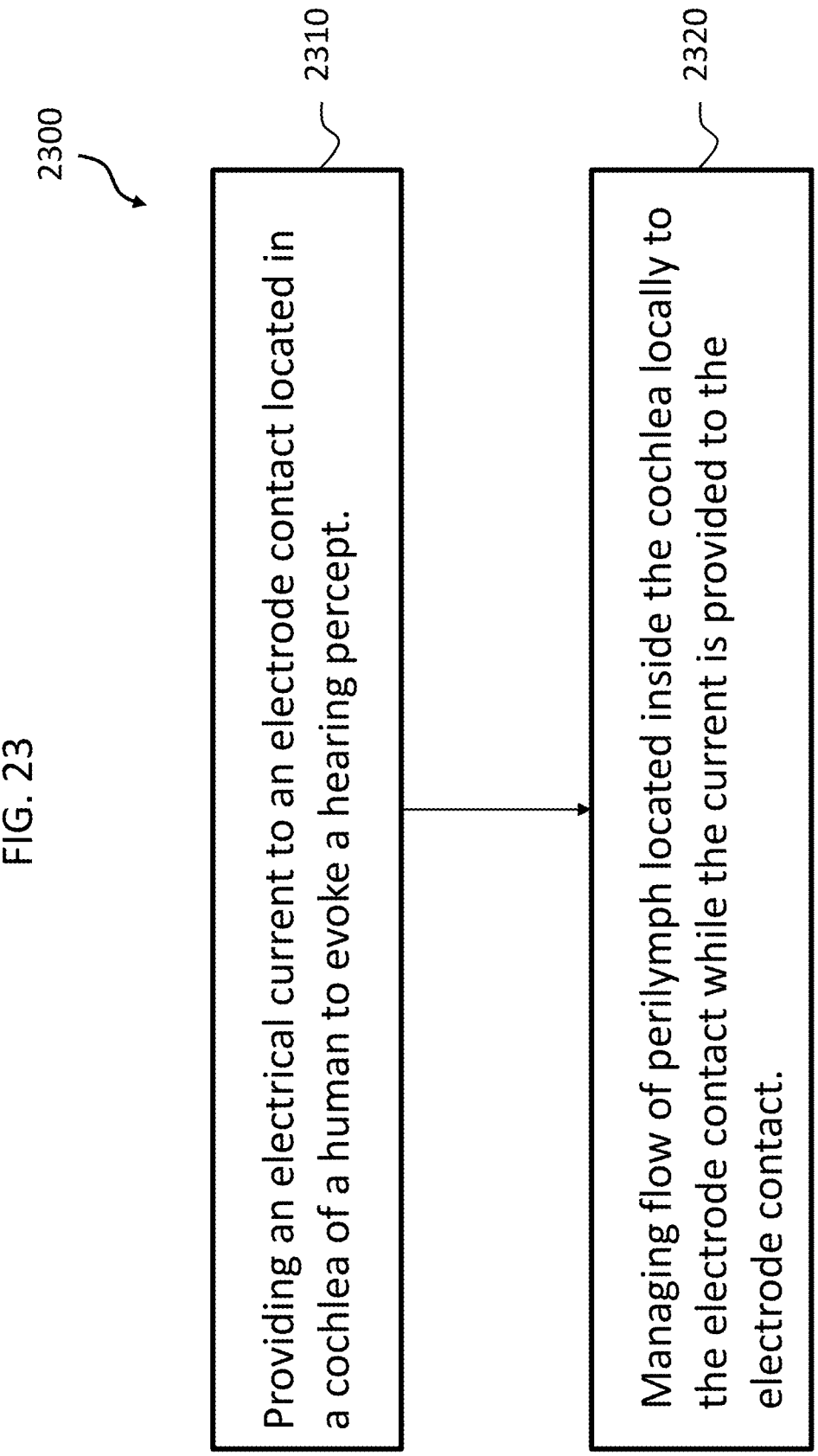
FIGS. 23 and 24 depict exemplary flowchart according to some exemplary embodiments.

FIG. 23 depicts a flowchart for an exemplary method, method 2300, according to an exemplary embodiment. Method 2300 includes method action 2310, which includes providing an electrical current to electrode contact located in a cochlea of a human to evoke a hearing percept. In an exemplary embodiment, this is done via the traditional method of applying a stimulation signal generated by an implanted receiver stimulator of a cochlear implant to a lead that extends from the receiver stimulator to the electrode contact. Method 2300 further includes method action 2320, which includes managing flow of perilymph located inside the cochlea while the current is provided to the electrode contact. In an exemplary embodiment, the action of managing the flow of perilymph corresponds to that which results from any of the techniques detailed herein and/or variations thereof. Some additional details of managing the flow of perilymph as applicable to this method represented by the flowchart of FIG. 23 will be described in greater detail below.

In an exemplary embodiment, method action 2320 include the action of locking flow of perilymph into and out of a volume located directly between the contact and the wall of the cochlea in a direction parallel to a tangent surface of the wall of the cochlea local to the contact. In an exemplary embodiment, this wall is the modiolus wall. Such method action is concomitant with FIGS. 21 and 22 above. As is to be understood with respect to, for example, the embodiments that utilize the squishy seal, the volume is a variable volume, which volume can vary with respect to the compressive forces applied by the electrode array onto the seal. Also concomitant with the teachings detailed above, in an exemplary embodiment, method 2320 is executed via the use of a seal between an electrode carrier of the electrode contact and a wall of the cochlea, which seal surrounds the contact.

Also consistent with the teachings of the above, in an exemplary embodiment, the contact that is an issue in method 2300 is part of an electrode array of a cochlear implant. Also consistent with the teachings of the above, in an exemplary embodiment, the electrode array that can be reinforced with a pre-curved stiffener. In an exemplary embodiment, this pre-curved stiffener can be elastic. This elastic pre-curved stiffener urges the electrode array against the wall of the cochlea (where, in some embodiments, such as those where the contacts and/or the carrier do not contact the wall of the cochlea, this means that the pre-curved stiffener urges the seals against the wall of the cochlea), thereby compressing a barrier surrounding the electrode contact located on the carrier against a wall of the cochlea. This compression is such that the barrier forms a seal between the electrode contact and the ambient environment, thereby managing the flow of perilymph.

In some exemplary embodiments, method action 2320 includes limiting flow of perilymph into and out of a volume that is solidly bounded everywhere by components of the electrode array, of which the electrode contact to which the electrical current provided in method action 2310 is a part, and a wall of the cochlea, such as by way of example only and not by way of limitation, the modiolus wall of the cochlea. Again, in some embodiments, the components of the electrode array that form the boundaries of the aforementioned volume include the barriers detailed herein, the contacts, and, in some instances, depending on the arrangements of the seal and/or the amount of compression of the seal, the carrier of the electrode contacts. This does not rule out other components, such as by way of example only and not by way of limitation, the aforementioned hard plastic components that are utilized in scenarios where the electrodes are held away from the modiolus wall a greater distance (the smokestack embodiment), which components are also components of the electrode array.

Still with reference to method action 2320, in an exemplary embodiment, the action of managing flow of perilymph is executed utilizing a squished component of an electrode array, such as by way of example only and not by way of limitation, the aforementioned silicone gel seals detailed herein and/or the foam seals detailed herein. In these exemplary embodiments, consistent with the teachings above, the squished components forms a barrier between a volume adjacent the electrode contact (e.g., above the surface of the electrode contact), and the ambient environment outside the volume.

It is noted that with reference to the volumes 874 established by the barriers detailed herein, in at least some exemplary embodiments, the size of the volumes 874 is a substantial function of a compression force on the seals that establish the boundary of the volumes. As noted above, in some exemplary embodiments, this compression force is a result of the pre-curved features of the electrode array. That said, alternatively and/or in addition to this, in an exemplary embodiment, the electrode arrays are configured so that they spanned the entire distance across the cochlea, from the modiolus wall to the lateral wall. In this regard, in an exemplary embodiment, an electrode array is configured such that structure is located against the lateral wall, which structure pushes the remainder of the electrode array against the modiolus wall, thus compressing the barriers. In an exemplary embodiment, a foam or the like can be utilized, which foam, in some embodiments, can substantially fill the duct of the cochlea in which the electrode array is located. In an exemplary embodiment, stilts or the like can be used. Any structure that can provide a compression force so that the seals are compressed to enable the teachings detailed herein can be utilized in at least some exemplary embodiments.

Figure 24:
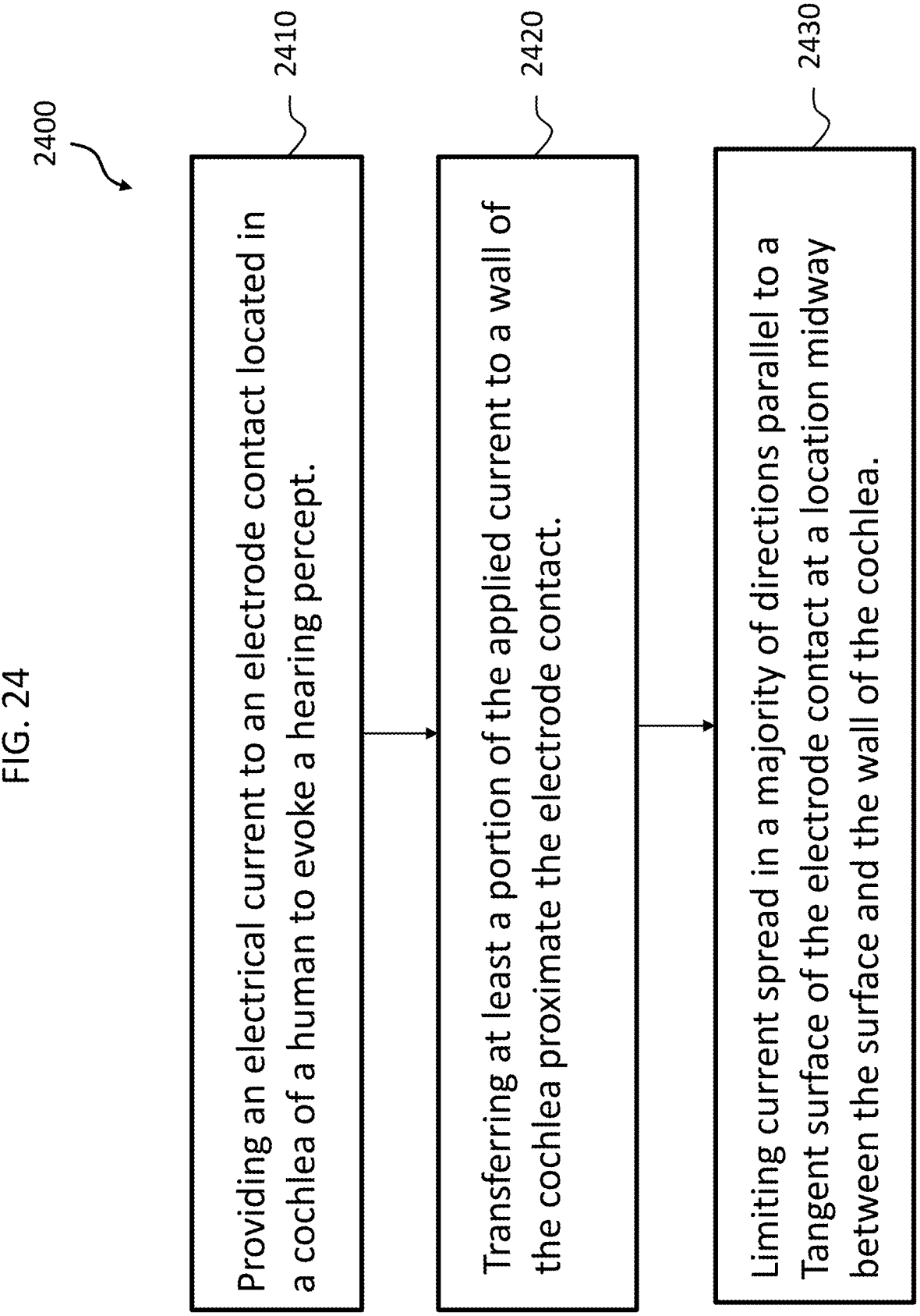
Figure 25:
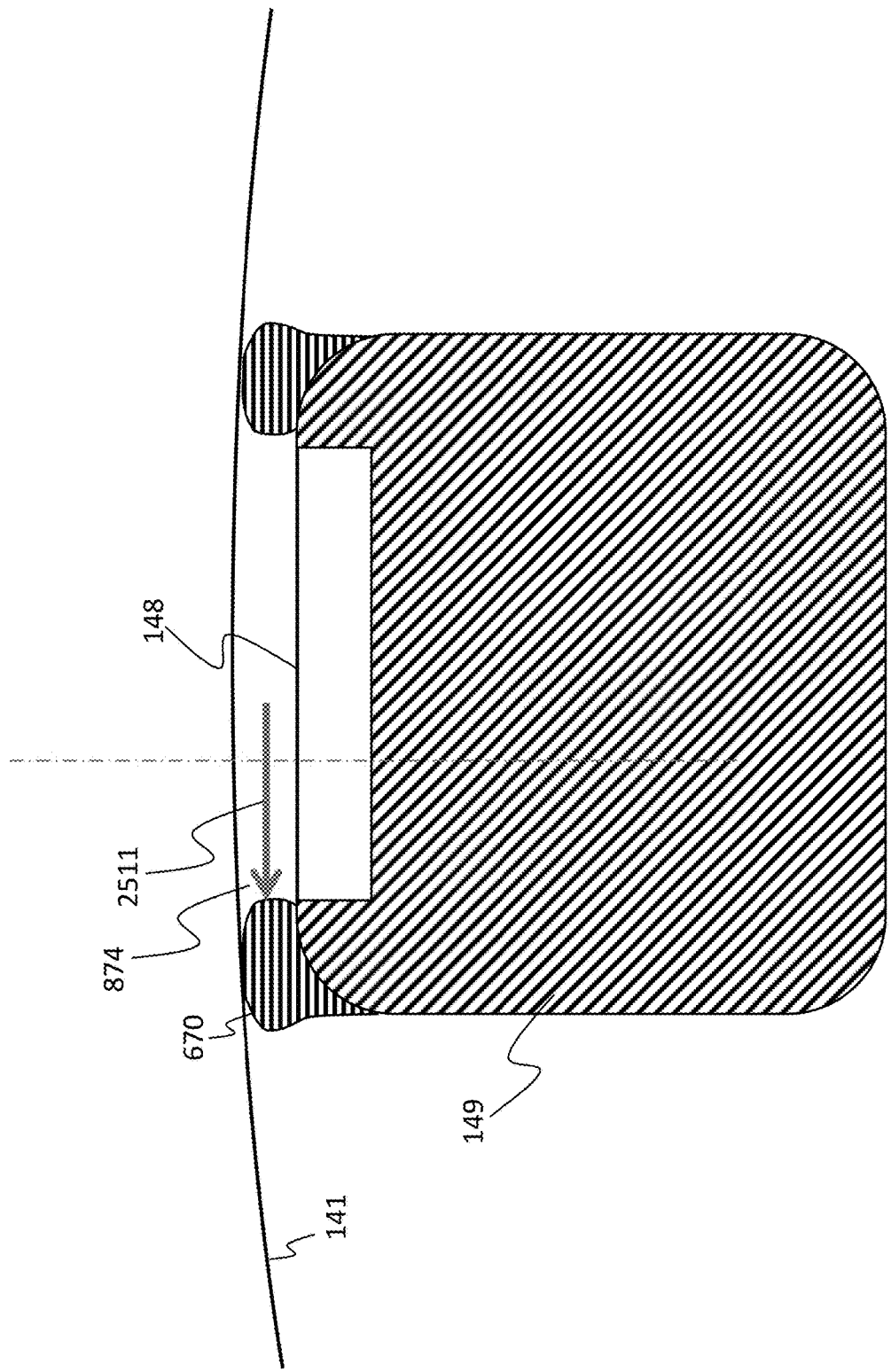
FIG. 25 depicts a cross-sectional view of an exemplary cochlear electrode array along with a portion of a wall of the cochlea, upon which is superimposed details of current travel.

FIG. 24 represents another exemplary flowchart for another exemplary method, method 2400, according to an exemplary embodiment. Method 2400 includes method action 2410, which includes providing an electrical current to electrode contact located in a cochlea of a human to evoke a hearing percept, the electrode contact being part of an electrode array of a cochlear implant. In this regard, method action 2410 is a more specific version of method action 2310 detailed above. Method 2400 further includes method action 2420, which includes transferring at least a portion of the applied current to a wall of the cochlea proximate the electrode contact. In an exemplary embodiment, this corresponds to the modiolus wall of the cochlea. Method 2400 further includes method action 2430, which includes limiting current spread in a majority of directions (which includes all directions) parallel to a tangent surface of the electrode contact at a location midway between the surface and the wall of the cochlea. In an exemplary embodiment, this corresponds to limiting current spread in a majority of directions normal to an axis most directly between the electrode contact and the wall of the cochlea via structure of the electrode array. FIG. 25 depicts this by way of exemplary schematic. As can be seen, there is an axis that is normal to the tangent surface of the electrode 148. Arrow 2511 represents current flow in a direction that is parallel to the tangent surface of the electrode contact. Arrow 2511 is located at a midpoint between the surface of the electrode 148 and the surface of the modiolus wall 141. While the embodiment of method 2400 is focused on the midpoint of the distance between the contact in the wall of the cochlea, in an alternate exemplary embodiment, the spread of current is limited at a location about 10%, 20%, 30%, 40%, 50%, 60%, 70%, 80%, 90%, 95%, 96%, 97%, 98%, or 99% of the way from the surface of the electrode contact to the wall of the cochlea. By "majority of directions parallel to a tangent surface of the electrode contact," it is meant, with reference to FIG. 21, now in terms of arrow 2111 representing current spread, directions summing to more than 180 degrees, whether contiguous or not contiguous. In an exemplary embodiment, as noted above, in at least some embodiments, the limiting of the current spread is done in all directions parallel to the tangent surface of the electrode contact, which means all values of A1 from 0 to 360°.

Figure 26:
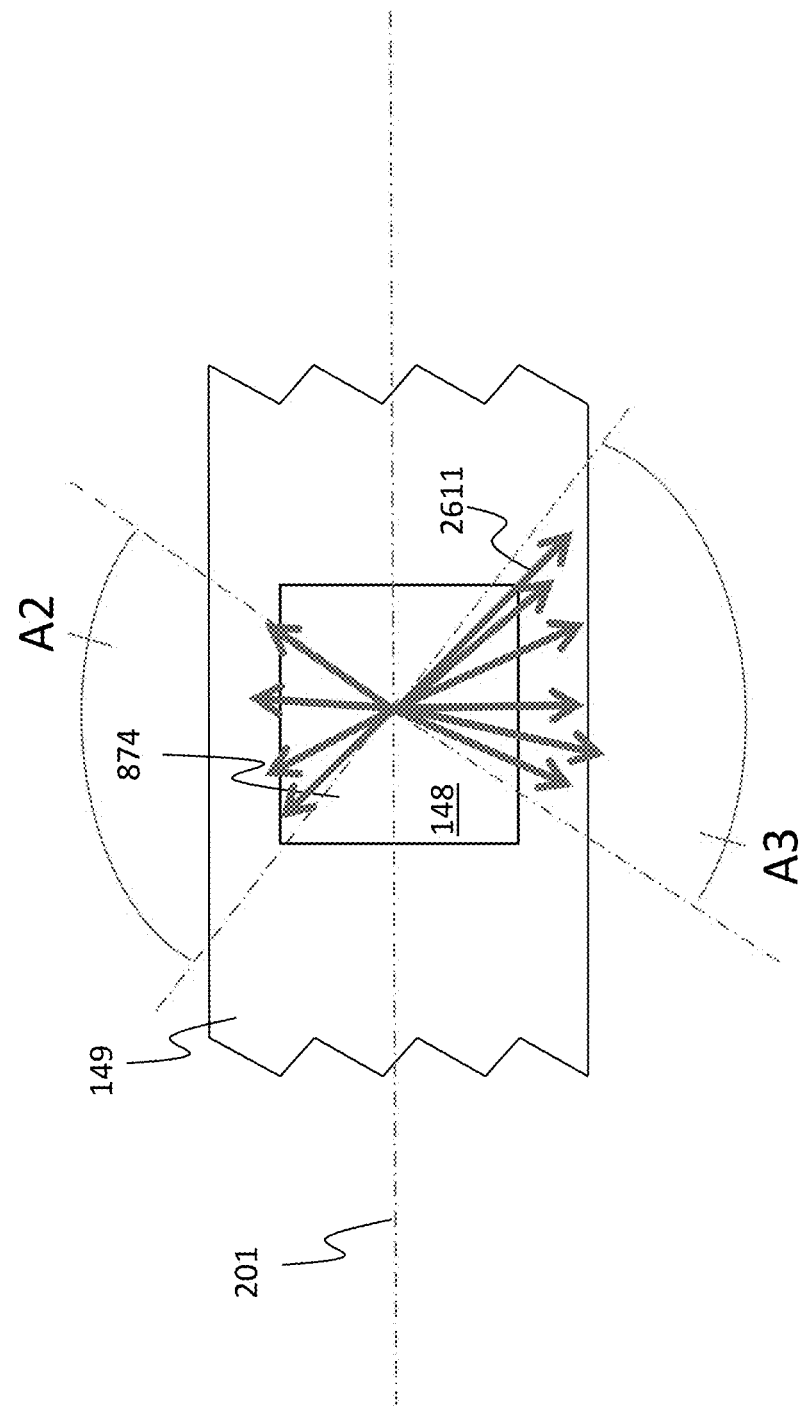
FIG. 26 is a top view of a portion of a cochlear electrode array upon which is superimposed some details associated with current travel.

In an exemplary embodiment of method action 2430, the limiting of the current spread is executed for directions, whether cumulative or not cumulative, by an amount that equals or is more than 180.1 degrees, 185 degrees, 190 degrees, 195, 200, 205, 210, 220, 225, 230, 235, 240, 245, 250, 255, 260, 265, 270, 275, 280, 285, 290, 295, 300, 305, 310, 320, 325, 330, 335, 340, 345, 350, 355, or 360 degrees, or any value or range of values therebetween in 0.05 degree increments. FIG. 26 conceptually depicts current spread in a plane parallel to the tangent surface of the electrode 148. While the current spread is represented by arrows 2611 that emanate from the same location on the electrode contact 148, it is to be understood that the current will emanate from multiple locations on the contact surface. In an exemplary embodiment, method action 2430 is executed such that the current spread is limited outside the angles A2 and A3. In an exemplary embodiment, A2 corresponds to 85 degrees, and A3 corresponds to 87 degrees. Thus, method action 2430 is executed such that current spread is limited, collectively, over a sum total of directions summing to 188 degrees. Again, the embodiment of FIG. 26 is simply for conceptual purposes.

Accordingly, in view of the above, in an exemplary embodiment, method action 2430 is such that the action of limiting current spread is executed for at least substantially all of the directions parallel to the tangent surface of the electrode contact at the aforementioned midpoint. Still further, in an exemplary embodiment, the action of limiting current spread is executed for all of directions parallel to the tangent surface.

In at least some exemplary embodiments, the above values (and the below values) with respect to the current flow can be also applicable to the perilymph flow (and vice versa).

In at least some exemplary embodiments, the limiting current spread is limited such that the current spread is no more than 5%, 10%, 15%, 20%, 25%, 30%, 35%, 40%, 45%, 50%, 55%, 60%, 65%, 70%, 75%, 80%, 85%, 90%, 95%, or any value or range of values therebetween in 0.1% increments of that which would be the case in the absence of structure of the electrode array above the outer surface of the electrode contact, all other things being equal. By "above the electrode contact," it is meant the material lying in a strata between the surface of the electrode array and the surface of the cochlea wall, which strata extends beyond the boundaries of the electrode contact. In an exemplary embodiment, such applicable structure can correspond to the structure of the barriers detailed herein and/or variations thereof. Any structure that inhibits the current spread according to the teachings detailed herein beyond that which would result in the absence of such structure can be utilized to execute this exemplary method action.

With respect to the action of limiting current spread, in at least some exemplary embodiments, the action of limiting current spread is executed at least indirectly by limiting flow of perilymph located in the cochlea into and/or out of the region proximate the electrode contact. In an exemplary embodiment, the limitation of flow is executed utilizing the barriers detailed above. In some exemplary embodiments, the action of limiting current spread is executed directly by limiting flow of perilymph located in the cochlea into and/or out of the region proximate the electrode contact. In an exemplary embodiment, the action of limiting perilymph flow is executed by forming a seal between the cochlea and the electrode contact, which seal is at least a portion of the structure of the electrode array.

In at least some exemplary embodiments, the action of limiting current spread is executed at least indirectly, which includes directly by trapping perilymph in a space between the electrode contact in the wall of the cochlea. In some exemplary embodiments, such trapping can be executed according to the teachings detailed above, such as by way of example only and not by way of limitation, utilizing the seals detailed above. Corollary to this is that in at least some exemplary embodiments, the action of limiting current spread is executed at least indirectly by electrically insulating perilymph located in a space between the electrode contact and the wall of the cochlea from perilymph outside the space, such as by way of example only and not by way of limitation, perilymph immediately on the opposite side of the seal located on the midpoint plane that is the subject of method action 2430. In an exemplary embodiment, the electrical resistance between the perilymph inside the space and the perilymph outside the space, is X ohms, where X can be 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 3000, 4000, 5000, 6000, 7000, 8000, 9000, or 10000 or more ohms or any value or range of values therebetween in about 1 ohm increments. In an exemplary embodiment, the aforementioned barriers detailed herein and/or variations thereof are such that a path of least electrical resistance from perilymph inside the volume 874 to perilymph outside the volume 874 and vice versa extends through the wall of the cochlea. In an exemplary embodiment, this path of least resistance is at least 20%, 25%, 30%, 35%, 40%, 45%, 50%, 55%, 60%, 65%, 70%, 75%, 80%, 85%, 90%, 95%, 96%, 97%, 98% or 99% or more or any value or range of values therebetween in 0.1% increments less resistive then the path in the direction parallel to the tangent surface of the electrode array noted above with respect to method action 2430 from the inside of the volume 874 to the outside of the barrier.

It is to be noted that in at least some exemplary embodiments, the teachings detailed herein can have utilitarian value with respect to increasing the number of effective frequency channels provided to the recipient. In at least some exemplary embodiments, the cochlear implants detailed herein have 22 channels, one channel for each electrode. In an exemplary embodiment, the electrodes are tonotopically mapped to the cochlea such that a given electrode stimulates a given frequency range of the cochlea in accordance with traditional mapping techniques. However, due to current spreading, effectively, such cochlear implants can only have, in some scenarios of use, less than 22 channels. In an exemplary embodiment, the cochlear implant has 8, 9, 10, 11, 12, 13, 14, 15, 16, 17, 18, 19, 20, 21, 22, 23, 24, 25, 26, 27, 28, 29, or 30, or more channels, and thus respective electrode contacts for each channel. However, the effective channels received by the recipient are only 2, 3, 4, 5, 6, 7, 8, 9, 10, 11, 12, 13, 14, 15, 16, 17, 18, 19, 20, 21, 22, 23, 24, or 25. In at least some exemplary embodiments, the action of evoking a hearing percept of method 2400 is part of a method that activates at least half of the channels of the cochlear implant (the action of evoking a hearing percept can span a period of seconds, minutes, and/or tens of minutes or more, and the action of evoking a hearing percept need not be contiguous). It is noted that in at least some exemplary embodiments, some channels will be deactivated and/or otherwise will not function due to various reasons. In an exemplary embodiment, the action of evoking a hearing percept of method 2400 is part of a method that activates at least 5, 6, 7, 8, 9, 10, 11, 12, 13, 14, 15, 16, 17, 18, 19, 20, 21, 22, 23, 24, 25, 26, 27, 28, 29, or 30 of the available channels of the cochlear implant depending on the scenario and/or the configuration of the cochlear implant.

In at least some exemplary embodiments, the action of evoking a hearing percept results from more effective channels of the cochlear implant than that which would be the case in the absence of structure of the electrode array above the outer surface of the electrode contact (e.g. the barriers detailed herein). By way of example only and not by way of limitation, 1, 2, 3, 4, 5, 6, 7, 8, 9, 10, 11, 12, 13 14, 15, 16, 17, 18, 19, 20, 21, 22, 23, 24, 25, 26, or more effective channels can result from method 2400 than that which would have been the case without the aforementioned structure.

By way of example only and not by way of limitation, there is a cochlear implant that includes at least X stimulating channels, where the respective stimulating channels have respective electrode contacts (one of which is the electrode contact to which current is provided a method 2400). The action of evoking the hearing percept as part of a method that activates at least Y of the at least X channels. In this exemplary method, the evoked hearing percept results from Z more effective channels of the cochlear implant than that which would be the case in the absence structure of the electrode array above the outer surface of the electrode contact. In an exemplary embodiment, X is any number of the group of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80 or any value or range of values therebetween in 1 increment, Y is any number of the group of 1, 2, 3, 4, 5, 6, 7, 8, 9, 10, 11, 12, 13, 14, 15, 16, 17, 18, 19, 20, 21, 22, 23, 24, 25, 26, 27, 28, 29, providing that Y is less than X, and Z is any number of the group of 1, 2, 3, 4, 5, 6, 7, 8, 9, 10, 11, 12, 13, 14, 15, 16, 17, 18, 19, 20, 21, 22, 23, 24, 25, 26, 27, 28, or 29, providing that the total number of effective channels does not exceed Y. By way of example only and not by way of limitation, in an exemplary embodiment, X is 15, Y is 7 and Z is 1 or more. In an exemplary embodiment, X is 15, Y is 10, and Z is at least a number that is W % more effective channels than that which would be the case in the absence of the structure of the electrode array above the outer surface of the electrode contact. In an exemplary embodiment, W is 2%, 5%, 7.5%, 10%, 15%, 20%, 25%, 30%, 35%, 40%, 45%, 50%, 55%, 60%, 70%, 80%, 90%, 100%, 115%, 130%, 145%, 160%, 180%, 200%, 225%, 250%, 275%, 300%, 325%, 350%, 375%, 400%, 450%, 500%, 550%, or 600%, or more or any value or range of values therebetween in 1% increments. In an exemplary embodiment, there is a cochlear electrode array that has 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105 or 110 or more or any value or range of values therebetween in 1 increment effective channels.

In at least some exemplary embodiments, because of the teachings detailed herein, the stimulation current that reaches the spiral ganglion cells is more concentrated than that which would be the case in the absence of the barriers detailed herein. By way of example and not by way of limitation, the area in which 80% of the stimulation current given off by an electrode contact that reaches the spiral ganglion cells is concentrated in an area that is no more than 90%, 85%, 80%, 75%, 70%, 65%, 60%, 55%, 50%, 45%, 40%, 35%, 30%, 25%, 20%, 15%, or 10%, or any value or range of values therebetween in 1% increments that which would result in the absence of the barriers detailed herein, all other things being equal. In an exemplary embodiment, the overlap of stimulated regions from neighboring electrodes is reduced by 2%, 5%, 7.5%, 10%, 15%, 20%, 25%, 30%, 35%, 40%, 45%, 50%, 55%, 60%, 70%, 80%, 90%, or even 100% or any value or range of values therebetween in 1% increments, relative to that which be the case in the absence of the barriers detailed herein.

It is noted that in at least some exemplary embodiments, the above is reproducible for multiple recipients. By way of example only and not by way of limitation, the methods detailed herein can be executed for at least 5, 6, 7, 8, 9, 10, 11, 12, 13, 14, 15, 16, 17, 18, 19, 20, 25, 30, 35, 40, 45, 50, 60, 70, 80, 90, 100, 125, 150, 200, 300, 400, 500, 600, 700, 800, 900, or 1000, or more recipients for respective number of times in temporal periods spanning 2 weeks, 4 weeks, 6 weeks, two months, three months, four months, five months, six months, 3 quarters, 4 quarters, 5 quarters, 6 quarters, 7 quarters, 8 quarters, 9 quarters, 10 quarters, 11 quarters, 12 quarters, 4 years, 5 years, or longer. By way of example only and not by way of limitation, in embodiments where the action of evoking a hearing percept results from at least, for example, 25% more effective channels of the cochlear implant than that which would have been the case in the absence of the teachings detailed herein, in an exemplary embodiment, that can be done for 10 different recipients respectively 10 times.

It is further noted that in at least some exemplary embodiments of the cochlear electrode arrays detailed herein, the respective current discharge area of the respective electrode contacts can be 0.05, 0.06, 0.07, 0.08, 0.08, 0.1, 0.15, 0.2, 0.25, 0.3, 0.35, 0.4, 0.45, 0.5, 0.55, 0.6. 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0 mm$^2$ or any value or range of values therebetween or less than thereof in 0.01 increments. By way of example only and not by way of limitation, with respect to the embodiment of FIG. 22, where the seal is compressed as shown, the current discharge area of the electrode 148 would be the entire surface of the electrode contact 148, because no portion of the upper surface of that contact is covered (where covered means that an insulative material, such as the seal and/or the carrier material, is in contact with the upper surface—this as opposed to a scenario where the seal overhangs the surface but does not contact that surface such that perilymph, for example, can be located underneath that overhang) by any insulative material. In an alternate embodiment, the respective current discharge area of the respective electrode contact, such as with reference to FIG. 12, would be the area between where the seal lips as compressed no longer contact the top surface of the electrode 148.

In an exemplary embodiment, irrespective of whether the electrode is covered or not by insulative material, in an exemplary embodiment, the top surface area of a respective electrode contact is 2 mm$^2$ or less or any value or range of values therebelow in 0.01 mm$^2$ increments.

In an exemplary embodiment, the charge density/current density during operation of the cochlear implant for a given electrode is 0.1 to 0.25 µA/µm$^2$ or any value or range of values tehrebetween in 0.001 µA/µm$^2$ increments. In an exemplary embodiment, the charge density is the same as or within 1, 2, 3, 4, 5, 6, 7, 8, 9, 10, 15, or 20% of the charge density utilized for standard cochlear implants.

Briefly, it is noted that the methods detailed herein these of the stimulating the cochlea to evoke a hearing percept are executed with perilymph located between the contacts and the wall of the cochlea. Indeed, in an exemplary embodiment, the volumes 874 are full of perilymph. In an exemplary embodiment, the cochlea is also full of perilymph when these method actions are executed. In an exemplary embodiment, all of the current that travels from the electrode contact to the wall of the cochlea travels through perilymph. In an exemplary embodiment, at least 50%, 55%, 60%, 65%, 70%, 75%, 80%, 85%, 90%, 91%, 92%, 93%, 94%, 95%, 96%, 97%, 98%, 99%, or more or any value or range of values therebetween in about 0.1% increments travels through perilymph to reach the cochlea.

In at least some exemplary embodiments of the barriers detailed herein, the barriers are configured so as to promote fibrous tissue growth with the barriers. In an exemplary embodiment, such as the methods detailed herein, the methods are executed where the tissue of the modiolus wall and/or lateral wall or other wall of the cochlear has ingrown at least partially with material of the barrier. In an exemplary embodiment, the barrier is configured to enhance such a growth.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, and it is not otherwise noted that such is not the case.

In an exemplary embodiment, there is an array as detailed above and/or below, wherein the carrier has a generally curved outer cross-section lying on a plane normal to a longitudinal axis of the electrode array; and the barriers have a cross-section lying on a plane normal to the longitudinal axis that has a top surface that is substantially flat in a relaxed state. In an exemplary embodiment, there is an array as detailed above and/or below, wherein the carrier has a generally curved outer cross-section lying on a plane normal to a longitudinal axis of the electrode array; and the barriers have a cross-section lying on a plane normal to the longitudinal axis that has a top surface that is curved in a relaxed state. In an exemplary embodiment, there is an array as detailed above and/or below, wherein the carrier has a generally curved outer cross-section lying on a plane normal to a longitudinal axis of the electrode array; and the barriers have a top surface that substantially lies in the same plane in a relaxed state. In an exemplary embodiment, there is an array as detailed above and/or below, wherein the carrier has a generally curved outer cross-section lying on a plane normal to a longitudinal axis of the electrode array; and the barriers have a top surface that substantially lies in an arcuate space in a relaxed state. In an exemplary embodiment, there is an array as detailed above and/or below, wherein the carrier has a generally rectangular outer cross-section lying on a plane normal to a longitudinal axis of the electrode array; and the barriers have a top surface that substantially lies in the same plane in a relaxed state. In an exemplary embodiment, there is an array as detailed above and/or below, wherein the carrier has a generally rectangular outer cross-section lying on a plane normal to a longitudinal axis of the electrode array; and the barriers have a top surface that substantially lies in an arcuate space in a relaxed state.

In an exemplary embodiment, there is a cochlear electrode array, comprising: an array of electrode contacts; a carrier carrying the array of electrode contacts; and respective barriers surrounding the electrode contacts.

In an exemplary embodiment, there is an array as detailed above and/or below, wherein the electrode array is a pre-curved perimodiolar electrode array; and the barriers limit ingress and egress of perilymph when the barriers are compressed against the modiolar wall. In an exemplary embodiment, there is an array as detailed above and/or below, wherein the carrier has a first durometer value, and the barrier has a second durometer value that is substantially lower than the first durometer value. In an exemplary embodiment, there is an array as detailed above and/or below, wherein the cochlear electrode array includes at least ten electrode contacts representing ten different channels of a cochlear implant; and a respective current discharge area of the respective electrode contacts of the at least ten electrode contacts is 0.1 $mm^2$ to 2.0 $mm^2$.

In an exemplary embodiment, there is a method, comprising providing an electrical current to an electrode contact located in a cochlea of a human to evoke a hearing percept, the electrode contact being part of an electrode array of a cochlear implant; transferring at least a portion of the applied current to a wall of the cochlea proximate the electrode contact; and limiting current spread in a majority of directions parallel to a tangent surface of the electrode contact at a location midway between the surface and the wall of the cochlea.

In an exemplary embodiment, there is a method as described above and/or below, wherein the action of limiting current spread is executed for all of the directions parallel to the tangent surface. In an exemplary embodiment, there is a method as described above and/or below, wherein the cochlear implant includes at least fifteen channels stimulating channels, respective stimulating channels having respective electrode contacts, one of which is the electrode contact to which the current is provided; the action of evoking the hearing percept is part of a method that activates at least ten of the at least fifteen channels; and the action of evoking the hearing percept results from at least 25% more effective channels of the cochlear implant than that which would be the case in the absence of structure of the electrode array above the outer surface of the electrode contact.

In an exemplary embodiment, there is a method as described above and/or below, wherein the action of limiting current spread is executed at least indirectly by electrically insulating perilymph located in a space between the electrode contact and the wall of the cochlea from perilymph outside the space. In an exemplary embodiment, there is a method as described above and/or below, wherein the action of limiting current spread is executed at least indirectly by trapping perilymph in a space between the electrode contact and the wall of the cochlea.

An embodiment includes cochlear electrode array, comprising an array of electrode contacts, a carrier carrying the array of electrode contacts and a plurality of barriers, wherein respective barriers of the plurality of barriers surround respective electrode contacts of a plurality of contacts of the array of contacts, wherein the respective electrode contacts have respective surfaces facing outboard relative to the cochlear electrode array that are located below crests of the respective barriers surrounding the respective electrode contacts.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. An implantable stimulating assembly, comprising:
an electrode contact;
an electrode carrier member carrying the electrode contact; and
a raised barrier extending above the carrier member and extending around the electrode contact on an outside of the carrier member, wherein
the barrier is configured to be urged against tissue of a recipient so that at least the tissue, the barrier and the electrode contact form a closed volume,
the barrier is configured to inhibit a flow of body fluids from outside the barrier to inside the barrier when the barrier is urged against the tissue, and
an area immediately above the electrode contact is exposed to the outside of the electrode carrier member.

2. The assembly of claim 1, wherein:
the implantable stimulating assembly is a cochlear electrode array.

3. The assembly of claim 1, wherein:
the barrier is a continuous lip on the carrier member.

4. The assembly of claim 1, wherein:
outer surfaces of the barrier and the electrode contact collectively form a crater on the carrier member.

5. The assembly of claim 1, wherein:
the barrier is one of a curved barrier or a rectangular barrier when viewed looking down on the electrode contact from outside the assembly.

6. The assembly of claim 1, wherein:
the electrode contact is a half-band electrode; and
the barrier surrounds the electrode contact such that a top surface of the barrier entirely lies in a same plane.

7. The assembly of claim 1, wherein:
the tissue is the inside of a cochlea; and
the fluid is perilymph.

8. The assembly of claim 1, wherein:
the implantable stimulating assembly is a cochlear implant electrode array;
the cochlear implant electrode array is a perimodiolar electrode array; and
the barrier prevents the electrode contact from contacting a modiolus wall of the cochlea.

9. The assembly of claim 1, wherein:
there are a plurality of electrode contacts supported by the electrode carrier member and a plurality of raised barriers extending above the carrier member, wherein all electrode contacts supported by the electrode carrier member have the barriers of the plurality of raised barriers respectively extending around respective electrode contacts on the outside of the carrier member.

10. The assembly of claim 1, wherein:
the implantable stimulating assembly is a cochlear electrode array;
there are a plurality of electrode contacts and a plurality of raised barriers extending above the carrier member, respective barriers of the plurality of raised barriers respectively extending around respective electrode contacts of the plurality of electrode contacts on an outside of the carrier member;
the respective barriers of the plurality of raised barriers are configured to be urged against the tissue of the recipient so that at least the tissue, the barrier and the electrode contact form respective closed volumes; and
the respective barriers of the plurality of raised barriers are configured to inhibit the flow of body fluids from outside the respective barriers of the plurality of raised barriers to inside the respective barriers of the plurality of raised barriers when the respective barriers of the plurality of raised barriers are urged against the tissue; and
all electrode contacts of the cochlear electrode array have the respective barriers respectively extending around the respective electrode contacts on the outside of the carrier member.

11. A cochlear electrode array, comprising:
a plurality of electrode contacts in an array of electrode contacts;
a carrier carrying the array of electrode contacts; and
a plurality of raised barriers, wherein respective barriers of the plurality of raised barriers surround respective electrode contacts of the plurality of contacts of the array of contacts, wherein
the respective electrode contacts have respective surfaces facing outwards towards an outside of the cochlear electrode array that are located below crests of the respective barriers surrounding the respective electrode contacts,
the electrode array is a perimodiolar electrode array,
the barriers prevent the electrode contacts from contacting a modiolus wall of the cochlea,
respective areas immediately above the respective electrode contacts are exposed to an outside of the carrier, and
the plurality of raised barriers extend above an outer surface of the carrier, the outer surface of the carrier being located between the plurality of electrode contacts.

12. The array of claim 11, wherein:
the cochlear electrode array resembles a tentacle of an octopus.

13. The array of claim 11, wherein:
the cochlear electrode array is configured so that only the barriers of the cochlear electrode array are configured to contact the modiolus wall of the cochlea when the electrode array is fully inserted into the cochlea.

14. The array of claim 11, wherein:
the carrier has a generally rectangular outer cross-section lying on a plane normal to a longitudinal axis of the electrode array; and
the barriers have a cross-section lying on a plane normal to the longitudinal axis that has a top surface that is curved in a relaxed state.

15. The array of claim 11, wherein:
the carrier has a generally rectangular outer cross-section lying on a plane normal to a longitudinal axis of the electrode array; and
the barriers have a cross-section lying on a plane normal to the longitudinal axis that has a top surface that is flat in a relaxed state.

16. The array of claim 11, wherein:
the respective electrode contacts are in bottoms of respective valleys established by the respective barriers.

17. The array of claim 11, wherein:
the respective areas above the respective electrode contacts of the plurality of electrode contacts are free of overhang by the respective barriers.

18. The array of claim 11, wherein:
all electrode contacts of the array have the barriers respectively surrounding respective electrode contacts.

19. A cochlear electrode array, comprising:
a plurality of electrode contacts in the arrangement of an array of electrode contacts;
a carrier carrying the array of electrode contacts; and
a plurality of raised barriers, wherein respective barriers of the plurality of raised barriers surround respective electrode contacts of the plurality of contacts of the array of contacts, wherein
the barriers of the plurality of raised barriers are configured to be squished against a wall of the cochlea so that the barriers of the plurality of raised barriers form seals between the respective electrode contacts and the ambient environment,
respective areas immediately above the respective electrode contacts are exposed to an outside of the carrier, and
the plurality of raised barriers extend above an outer surface of the carrier, the outer surface of the carrier being located between the plurality of electrode contacts.

20. The array of claim 19, wherein:
all electrode contacts of the array have the barriers respectively surrounding respective electrode contacts.

21. The array of claim 19, wherein:
the electrode array is a perimodiolar electrode array; and
the barriers prevent the electrode contacts from contacting the cochlea.

22. The array of claim 19, wherein:
the cochlear electrode array resembles a tentacle of an octopus.

23. The array of claim 19, wherein:
the cochlear electrode array is configured so that only the barriers of the cochlear electrode array are configured to contact a modiolus wall of the cochlea when the cochlear electrode array is fully inserted into the cochlea.

24. The array of claim 19, wherein:
the carrier has a generally rectangular outer cross-section lying on a plane normal to a longitudinal axis of the electrode array; and
the barriers have a cross-section lying on a plane normal to the longitudinal axis that has a top surface that is curved in a relaxed state.

25. The array of claim 19, wherein:
the carrier has a generally rectangular outer cross-section lying on a plane normal to a longitudinal axis of the electrode array; and
the barriers have a cross-section lying on a plane normal to the longitudinal axis that has a top surface that is flat in a relaxed state.

26. An implantable stimulating assembly, comprising:
a plurality of metal electrode contacts;
an electrode carrier member carrying the metal electrode contacts; and
respective raised barriers extending around respective electrode contacts of the plurality of electrode contacts on an outside of the carrier member, wherein
an area immediately above the electrode contacts is exposed to the outside of the electrode carrier member,
all electrode contacts of the plurality of electrode contacts supported by the electrode carrier member have the respective barriers respectively extending around respective electrode contacts on the outside of the carrier member, and
the implantable assembly is a cochlear implant electrode array configured so that only the barriers of the implantable assembly are configured to contact a modiolus wall of a cochlea when the implantable assembly is fully inserted into the cochlea, and
the plurality of raised barriers extend above an outer surface of the electrode carrier member, the outer surface of the electrode carrier member being located between the plurality of electrode contacts.

27. The assembly of claim 26, wherein:
the assembly is a perimodiolar electrode array; and
the barriers prevent the electrode contacts from contacting the cochlea.

28. The assembly of claim 26, wherein:
the electrode carrier member has a generally rectangular outer cross-section lying on a plane normal to a longitudinal axis of the electrode carrier member; and
the barriers have a cross-section lying on a plane normal to the longitudinal axis that has a top surface that is curved in a relaxed state.

29. The assembly of claim 26, wherein:
the electrode carrier member has a generally rectangular outer cross-section lying on a plane normal to a longitudinal axis of the carrier member; and
the barriers have a cross-section lying on a plane normal to the longitudinal axis that has a top surface that is flat in a relaxed state.

\* \* \* \* \*